US008592169B2

(12) United States Patent
Robertson et al.

(10) Patent No.: US 8,592,169 B2
(45) Date of Patent: Nov. 26, 2013

(54) TUMOUR MARKER PROTEINS AND USES THEREOF

(75) Inventors: John Forsyth Russell Robertson, Nottingham (GB); Catherine Rosamund Louise Graves, Nottingham (GB)

(73) Assignee: Oncimmune Limited, Nottingham (GB)

( * ) Notice: Subject to any disclaimer, the term of this patent is extended or adjusted under 35 U.S.C. 154(b) by 0 days.

(21) Appl. No.: 10/534,773

(22) PCT Filed: Nov. 13, 2003

(86) PCT No.: PCT/GB03/04950
§ 371 (c)(1),
(2), (4) Date: May 13, 2005

(87) PCT Pub. No.: WO2004/044590
PCT Pub. Date: May 27, 2004

(65) Prior Publication Data
US 2006/0094069 A1   May 4, 2006

(30) Foreign Application Priority Data

Nov. 14, 2002 (GB) .................................. 0226622.9

(51) Int. Cl.
*G01N 33/574* (2006.01)
(52) U.S. Cl.
USPC ........................................................ 435/7.23
(58) Field of Classification Search
USPC ........................................................ 435/7.23
See application file for complete search history.

(56) References Cited

U.S. PATENT DOCUMENTS

| | | | |
|---|---|---|---|
| 4,898,951 A | 2/1990 | Symons | |
| 4,937,185 A | 6/1990 | Webb et al. | |
| 5,157,020 A | 10/1992 | Kay et al. | |
| 5,501,955 A | 3/1996 | Bergman | |
| 5,561,049 A | 10/1996 | Vold et al. | |
| 5,652,115 A | 7/1997 | Marks et al. | |
| 5,721,105 A | 2/1998 | Bergmann | |
| 5,726,023 A | 3/1998 | Cheever et al. | |
| 5,747,268 A | 5/1998 | Herring et al. | |
| 5,763,164 A | 6/1998 | Calenoff | |
| 5,876,728 A | 3/1999 | Kass et al. | |
| 5,885,793 A | 3/1999 | Griffiths et al. | |
| 6,187,306 B1 | 2/2001 | Pardoll et al. | |
| 6,280,962 B1 | 8/2001 | Cohen | |
| 6,322,989 B1 | 11/2001 | Cohen | |
| 6,387,639 B1 | 5/2002 | Posner et al. | |
| 6,475,804 B1 | 11/2002 | Lohse | |
| 6,645,465 B2 | 11/2003 | Hanash et al. | |
| 6,667,160 B2 | 12/2003 | Fine | |
| 7,282,345 B1 | 10/2007 | Hancock et al. | |
| 7,402,403 B1* | 7/2008 | Robertson et al. ............ 435/7.8 |
| 8,114,604 B2 | 2/2012 | Robertson et al. | |
| 2002/0168696 A1 | 11/2002 | Hanash | |
| 2003/0008332 A1 | 1/2003 | Ryan et al. | |
| 2003/0049692 A1 | 3/2003 | Latov et al. | |
| 2003/0099639 A1 | 5/2003 | Rikihisa et al. | |
| 2003/0138860 A1* | 7/2003 | Robertson et al. ........... 435/7.23 |
| 2003/0232399 A1* | 12/2003 | Robertson et al. ........... 435/7.23 |
| 2005/0084904 A1 | 4/2005 | Laal et al. | |
| 2005/0276485 A1 | 12/2005 | Mori | |
| 2006/0141547 A1 | 6/2006 | Das et al. | |
| 2007/0172487 A1 | 7/2007 | Shih et al. | |
| 2007/0224174 A1 | 9/2007 | Kang et al. | |
| 2008/0108084 A1 | 5/2008 | Robertson et al. | |
| 2008/0153113 A1 | 6/2008 | Robertson et al. | |
| 2008/0213921 A1 | 9/2008 | Robertson et al. | |
| 2008/0305476 A1 | 12/2008 | Robertson et al. | |
| 2009/0176319 A1* | 7/2009 | Robertson et al. ............ 436/518 |
| 2011/0086061 A1 | 4/2011 | Robertson et al. | |
| 2012/0115749 A1 | 5/2012 | Robertson et al. | |
| 2013/0090251 A1 | 4/2013 | Robertson et al. | |

FOREIGN PATENT DOCUMENTS

| | | |
|---|---|---|
| EP | 0 236 606 | 6/1992 |
| EP | 0684477 | 11/1995 |
| EP | 1200832 | 5/2006 |
| GB | 2395270 | 5/2004 |
| GB | 2395270 A | 5/2004 |
| GB | 2426581 | 11/2006 |
| JP | 7294530 | 11/1995 |
| JP | 09-189702 | 7/1997 |
| JP | 11-230966 | 8/1999 |
| WO | WO-89/01153 | 2/1989 |
| WO | WO 92/13065 | 8/1992 |
| WO | WO 93/11236 | 6/1993 |
| WO | WO 93/21529 | 10/1993 |
| WO | WO 94/23728 | 10/1994 |

(Continued)

OTHER PUBLICATIONS

Luo et al. (British J. Cancer 87:339-343 (2002)).*
Stedman's Medical Dictionary definition of "fluid"—pp. 1-2.*
Stockert et al. (J. Exp. Med. 1998; 187: 1349-1354).*
Zhang et al. (Cancer Epidemiology, Biomarkers & Prevention 2003; 12: 136-143).*
Casiano et al. (Molecular & Cellular Proteomics 2006; 5: 1745-1759).*
Steiber et al. (Cancer 1993; 72: 707-713).*
Muraki et al. (Cancer 1996, 77: 1274-1277).*
Brichory et al. (PNAS 2001: 98; 9824-9829).*
Treon et al. (Blood 96(6):3147-3153 (2000)).*

(Continued)

*Primary Examiner* — Lynn Bristol
(74) *Attorney, Agent, or Firm* — Kilpatrick Townsend & Stockton LLP

(57) ABSTRACT

The invention relates to tumor marker proteins and their preparation from fluids from one or more cancer patients, wherein said fluids are those which collect in a body cavity or space which is naturally occurring or which is the result of cancer or medical intervention for cancer. The invention also relates to preparation of tumor marker proteins from excretions taken from patients with cancer. The tumor marker proteins are useful as immunoassay reagents in the detection of cancer-associated anti-tumor marker autoantibodies.

54 Claims, 12 Drawing Sheets

(56) References Cited

FOREIGN PATENT DOCUMENTS

| WO | WO 96/00084 | | 1/1996 |
|---|---|---|---|
| WO | WO 96/03502 A2 | | 2/1996 |
| WO | 97/11715 | | 4/1997 |
| WO | WO 97/14794 | | 4/1997 |
| WO | WO-98/55872 | | 12/1998 |
| WO | WO 99/58978 | * | 11/1999 |
| WO | WO-99/58978 A2 | | 11/1999 |
| WO | WO 00/26668 | | 5/2000 |
| WO | WO-00/34787 | | 6/2000 |
| WO | WO-0111372 | | 2/2001 |
| WO | WO-02059617 | | 8/2002 |
| WO | WO 2008/032084 | | 9/2007 |

OTHER PUBLICATIONS

Szekanecz et al. (Ann. NY Acad Sci 1108:359-371 (2007) Abstract).*
Lederman et al (Molecular Immunology 28:1171-1181, 1991).*
Li et al (Proc. Natl. Acad. Sci. USA 77:3211-3214, 1980).*
Hirasawa et al. ("Natural Autoantibody to MUC1 Is a Prognostic Indicator for Non-Small Cell Lung Cancer" Am J Respir Crit Care Med 2000;161:589-594).*
Coomber et al. ("Characterisation and clinicopathological correlates of serum anti-p53 antibodies in breast and colon cancer" J Cancer Res Clin Oncol. 1996;122(12):757-62).*
Angelopoulou et al. ("Detection of the TP53 tumour suppressor gene product and p53 auto-antibodies in the ascites of women with ovarian cancer" European Journal of Cancer vol. 33, Issue 1, Jan. 1997, pp. 115-121).*
Aparecida et al., "Value of CEA Level Determination in Gallbladder Bile in the Diagnosis of Liver Metastases Secondary to Colorectal Adenocarcinoma", Sao Paulo Medical Journal, 2001, vol. 119, No. 3, pp. 110-113.
Apostolopoulos et al., Nature Medicine, 1998, vol. 4, pp. 315-320.
Baechstrom, et al., "Purification and Characterization of Sialyl-Le—Carrying Mucins of Human Bile; Evidence for the Presence of MUC1 and MUC3 Apoproteins", The Journal of Biological Chemistry, 1994, vol. 269, No. 20, pp. 14430-14437.
Beatty, et al., "Biochemical Characterization of the Soluble Form of Tumor Antigen MUC1 Isolated from Sera and Ascites Fluid of Breast and Pancreatic Cancer Patients", Clinical Cancer Research, 2001, vol. 7, pp. 781-787.
Ben-Mahrez et al., British Journal of Cancer, 1988.
Bhatti et al.; Journal of Tumor Marker Oncology, Summer-1994, vol. 9, pp. 125-131.
Croce et al.; Cancer. Immunol. Immunother., 1995, vol. 40, pp. 132-137.
Deguchi et al.; Int. Arch. Allergy Appl. Immunol., 1988, vol. 87, pp. 313-316.
Denton et al.; Cancer Letters, 1993, vol. 70, pp. 143-150.
Disis et al.; Journal of Clinical Oncology, 1997, vol. 15, pp. 3363-3367.
Fishman, P., "Application of autoantibodies to cancer therapy: A new concept", The 9$^{th}$ International Congress of Immunology, 1995, p. 664.
Gourevitch, MM; "Polymorphic epithelial mucin (MUC-1)-containing circulating immune complexes in carcinoma patients"; British Journal of Cancer; 72, pp. 934-938; (1995).
Green et al.; European Journal of Cancer, 1994, vol. 30A, pp. 580-584.
Güre, "Human Lung Cancer Antigens Recognized by Autologous Antibodies Definition of a Novel cDNA Derived from the Tumor Suppressor Gene Locus on Chromosome 3p21.3", Ludwig Institute for Cancer Research, pp. 1034-1040.
Abstract of Hayes; Anticancer Drugs, 1995, vol. 6, suppl. 2, pp. 26-27.
Hehir et al., Journal of Surgical Oncology, 1993, vol. 54, pp. 207-210.
Hill et al., "Nature of Carcinoembryonic Antigen Purified From Malignant Ascitic Fluid of Serous Cystadenocarcinoma of the Ovary", Molecular Immunology, 1981, vol. 18, No. 7, pp. 647-653.

Hinoda, et al., "Detection of a Circulating Antibody Against a Peptide Epitope on a Mucin Core Protein, MUC1, in Ulcerative Colitis", 1991, pp. 163-168.
Houghton et al.; "Detection of Cell Surface and Intracellular Antigens by Human Monoclonal Antibodies—Hybrid Cell Lines Derived from Lymphocytes of Patients with Malignant Melanoma"; J. Exp. Med.; vol. 158, Jul. 1983; pp. 53-65.
Janeway et al., Immunobiology, 5$^{th}$ ed.
Karanikas, et al. J Clin Invest Dec. 1, 1997 vol. 100, No. 11, pp. 2783-2792.
Kawahara; Cancer, 1986, vol. 58, pp. 2008-2012.
Kotera et al.; Cancer Research, 1994, vol. 54, pp. 2856-2860.
Kuralay, et al., Diagnostic Usefulness of Tumour Marker Levels in Pleural Effusions of Malignant and Benign Origin, Clinica Chimica Acta, 2000, vol. 300, pp. 43-55.
Kutteh, W.H., et al., "Immunologic characterization of tumor markers in human ovarian cancer cell lines"; Journal of the Society for Gynecologic Investigation, 1996, vol. 3, No. 4, pp. 216-222.
Laeng, et al., "Anti-Neural Autoantibodies, types 1 and 2: Their Utility in the Study of Tumors of the Nervous System", Acta Neuropathol, 1998, vol. 96, pp. 329-339.
Lafond, R.E., et al., "Autoantibodies to c-myc protein: elevated levels in patients with African Burkitt's lymphoma and normal Ghanians", Autoimmunity, vol. 13, No. 3, 1992, pp. 215-224.
Lai, et al., "Presence of Serum Anti-P53 Antibodies is Associated with Pleural Effusions and Poor Prognosis in Lung Cancer Patients", Clinical Cancer Research, 1998, vol. 4, pp. 3025-3030.
Lawniczak, et al., "The Search for Tumor-Associated Proteins in Pleural Effusions by Means of Monoclonal Antibodies and a Dot Blot Assay", Lung, 1992, vol. 170, pp. 65-74.
Mercer, "Use of Multiple Markers to Enhance Clinical Utility", Immunology Series, vol. 53, 1990, pp. 39-54.
Montenarh, et al., "P53 Autoantibodies in the Sera, Cyst and Ascitic Fluids of Patients with Ovarian Cancer", International Journal of Oncology, 1998, vol. 13, pp. 605-610.
Nery, et al., "Isolation and Partial Characterization of Macromolecular Urinary Aggregates Containing Carcinoembryonic Antigen-Like Activity", Br J. Cancer, 1974, vol. 29, No. 413.
Nustad et al., "Epitopes on CA 125 from Cervical Mucus and Ascites Fluid and Characterization of Six New Antibodies", pp. 303-314.
Abstract of Pandha et al.; Cancer Gene Therapy, 1997, vol. 4, No. 5, p. 310.
Pavelic et al., Anticancer Reasearch, 1991, vol. 11, pp. 1421-1428.
Petrarca, C., "Human Antibodies Against the Polymorphic Epithelial Mucin in Ovarian Cancer Patients Recognise a Novel Sequence in the Tandem Repeat Region"; European Journal of Cancer, vol. 32A, No. 12, pp. 2155-2163, 1996.
Petrakou et al.; International Journal of oncology, 1997, vol. 11, suppl. p. 902.
Rao, S.G., "Detection of Human Ovarian Tumor Associated Antigens by Autologous Antibodies Isolated from Ovarian Carcinoma Ascites Fluid"; Proceedings of the American Association for Cancer Research Annual Meeting, 1987, vol. 28, p. 358.
Rusciano, "Concomitant Purification of Prostatic Carcinoma Tumor Markers from Human Seminal Fluid Under Nondenaturing Conditions", Clinical Chemistry, 1988, vol. 34, No. 12, pp. 2528-2532.
Sahin et al.; PNAS, 1995, vol. 92, pp. 11810-11813.
Sandrin et al., Glycoconjugate Journal, 1997, vol. 14, pp. 97-105.
Scanlan et al.; International Journal of Cancer, 1998, vol. 76, pp. 652-658.
Schneider, J. "P53 Protein, EGF Receptor, and Anti-P53 Antibodies in Serum from Patients with Occupationally Derived Lung Cancer", British Journal of Cancer, 1999, vol. 80, No. 12, pp. 1987-1994.
Shibata, et al., "Purification and Characterization of Prostate Specific Antigen from Human Urine", Biochimica et Biophysica Acta, 1997, vol. 1336, pp. 425-433.
Sokoloff, et al., "A Dual-Monoclonal Sandwich Assay for Prostate-Specific Membrane Antigen: Levels in Tissues, Seminal Fluid and Urine", The Prostate, 2000, vol. 43, pp. 150-157.
Abstract of Stearns et al.; Breast Cancer Research and Treatment, Feb. 8, 1998, vol. 52, pp. 239-259.

(56) References Cited

OTHER PUBLICATIONS

Stubbs, et al., "Faecal Carcinoembryonic Antigen (CEA) in Patients with Large Bowel Cancer", European Journal of Surgical Oncology, 1987, vol. 13, pp. 433-436.

Tondini, et al., "Comparikni of CA15-3 and Carcinoembryonic Antigen in Monitoring the Clinical Course of Patients with Metastatic Breast Cancer", Cancer Research, 1988, vol. 48, No. 14, pp. 4107-4112.

Toth, et al., "A Carcinoembryonic Antigen (CEA) Binding Protein From Ascites Influences CEA Uptake by Macrophages", 1990, vol. 171, No. 2, pp. 633-640.

Venegas, et al., "Purificaton and Immunochemical Characterization of Ascitic Fluid Glycoproteins Containing Certain Tumor-Associated and Blood Group Antigen Markers", Glycoconjugate Journal, 1989, vol. 6, pp. 511-524.

Voet et al., Biochemistry, 1990, pp. 1096 and 1098.

Voet et al., Biochemistry, 1990, p. 78.

Volkmann, M., et al., "Anti-p53 autoantibodies as serological marker in different tumor-entities", Clinical Chemistry, vol. 41, No. S6 part 2, 1995, pp. S221-S222.

Abstract of Von Mensdorf-Pouilly et al.; Anticancer Research, Nov.-Dec. 1997, vol. 17, p. 4184.

Von Mensdorff-Pouilly, S., "Humoral Immune Response to Polymorphic Epithelial Mucin (MUC-1) inpatients with Benign and Malignant Breast Tumours"; European Journal of Cancer, vol. 32A, No. 8, pp. 1325-1331, 1996.

Wolf, et al., "A Tumour-Associated Antigen from the Pleural Effusion of Patients with Squamous-Cell Carcinoma of Lung", Br. J. Cancer, 1978, vol. 36, pp. 1046-1052.

Abstract of Yamamoto et al.; Proc. Amer. Soc. Cancer Res., Mar. 1997, p. 564.

Yamamoto et al., "L-Myc Overexpression and Detection of Auto-Antibodies Against L-Myc in Both the Serum and Pleural Effusion from a Patient with Non-Small Cell Lung Cancer", Internal Medicine, 1997, vol. 36, No. 10, pp. 724-727.

Yamauchi, et al., "Autoantibodies to C-MYC Nuclear Protein Products in Autoimmune Disease", 1989, pp. 117-119.

Zisman et al.; Journal of Urology, 1995, vol. 154, pp. 1052-1055.

Definition of "moncyte" in On-line Medical Dictionary downloaded on Feb. 5, 2005 from url..cancerweb.ncl.ac.uk.

Aaronson, S. A. et al., "Characterization of Murine Sarcoma Virus (KIRSTEN) Transformation of Mouse and Human Cells", J. Gen. Virol. 1971, 13: 245-252; 245-252.

Agrawal, et al., "Cancer-associated MUC1 mucin inhibits human T-cell proliferation, which is reversible by IL-2", Nature Medicine Jan. 1998, vol. 4, No. 1, 43-49.

Ambrosini, G. et al., "A novel anti-apoptois gene, survivin, expressed in cancer and lymphoma", Nature Med 1997, 3(8), 917-21.

Angelopoulou, K. et al., "Detection of the TP53 Tumour Suppressor Gene Product and p53 Auto-antibodies in the Ascites of Women with Ovarian Cancer", European Journal of Cancer Jan. 1997, Pergamon Press, Oxford, GB, vol. 33, No. 1, 115-121.

Anker, et al., "K-ras mutations are found in DNA extracted from the plasma of patients with colorectal cancer", Gastroenterology Apr. 1997, vol. 112, No. 4, 1114-1120.

Ayala, A. R. et al., "Human Chorionic Gonadotropin Immunoreactivity in Serum of Patients With Malignant Neoplasms", Am J Reprod Immuno. Apr.-May 1983, 3(3), 149-51.

Barak, V. et al., "Clinical utility of cytokeratins as tumor markers", Clin Biochem Jul. 2004, 37(7), 529-40.

Baselga, J. et al., "Phase II Study of Weekly Intravenous Recombinant Humanized Anti-p185 HER2 Monoclonal Antibody in Patients with HER2/neu-Overexpressing Metastatic Breast Cancer", J. Clin Oncol. 1996, 14(3), 737-744.

Beatty, J. D. et al., "Measurement of monoclonal antibody affinity by non-competitive enzyme immunoassay", Journal of Immunological Methods 1987, 100, 173-179.

Block, T. M. et al., "Use of targeted glycoproteomics to identify serum glycoproteins that correlate with liver cancer in woodchucks and humans", PNAS Jan. 18, 2005, 102(3), 779-84.

Booyse, F. M. et al., "Isolation and characterization of a urokinase-type plasminogen activator (MR = 54,000) from cultured human epithelial cells indistringuishable from urinary urokinase", J Biol Chem 1984, 259(11), 7198-205.

Braun, S. et al., "Cytokeratin-Positive Cells in the Bone Marrow and Survival of Patients with Stage I, II, or III Breast Cancer", N Engl J. Med 2000, 342:8, 525-533.

Callans, L. S. et al., "Raf-1 Protein Expression in Human Breast Cancer Cells", Ann Surg Oncol Jan. 1995, 2(1):38-42.

Carlsson, Hans E. "Titration of antibodies to Salmonella O Antigens by Enzyme-Linked Immunosorbent Assay", Infection and Immunity Nov. 1972, vol. 6, No. 5, 703-708.

Chari, S. et al., "Partial-Purification of Inhibin from Human Testicular Extracts", ACTA Endocrinologica 1977, 85 Suppl 212, 215-219.

Chen, Y. T. "A testicular antigen aberrantly expressed in human cancers detected by autologous antibody screening", PNAS 1997, 94, 1914-1918.

Chinni, R. S. et al., "Humoral Immune Responses to Cathepsin D and Glucose-regulated Protein 78 in Ovarian Cancer Patients", Clinical Cancer Research Sep. 1997, 3, 1557-1564.

Clemmensen, I. et al., "Purification and characterization of a novel, oligomeric, plasminogen kringle 4 binding-protein from human plasma-tetranectin", Eur J. Biochem 1986, 156(2), 327-333.

Coussens, L. et al., "Tyrosine kinase receptor with extensive homology to EGF receptor shares chromosomal location with neu oncogene", Science 1985, 230, 1132-1139.

Dahlberg, T. "Enzyme-Linked Immunosorbent Assay for Titration of Haemophilus influenzae Capsular and O Antigen Antibodies", Journal of Clinical Microbiology Aug. 1980, vol. 12, No. 2, 185-192.

Devine, P. L. et al., "Circulating Mucins as Tumor Markers in Ovarian Cancer (Review)", Anticancer Res. May-Jun. 1992, 12(3), 709-17.

Diamandis, E. P. et al., "Human Tissue Kallikreins: A Family of New Cancer Biomarkers", Clin. Chem Aug. 2002, 48(8), 1198-1205.

Diamandis, et al., "The new human kallikrein gene family: implications in carcinogenesis", Trends Endocrinol Metab. 11(2) Mar. 2000, 54-60.

Downward, et al., "Close similarity of epidermal growth factor receptor and v-erb-B oncogene protein sequences", Nature 1984, 307, 521-527.

Ellis, I. O. et al., "A monoclonal antibody, NCRC-11, raised to human breast carcinoma. 1. Production and immunohistological characterization", Histopathology 1984, 8: 501-516.

Fernandez-Madrid, F. "Autoantibodies to Annexin XI-A and Other Autoantigens in the Diagnosis of Breast Cancer", Cancer Research 2004, 64, 5089-5096.

Fossa, A. et al., "Identification of a nucleolar protein No55 as a tumour-associated auto-antigen in patients with prostate cancer", Br J Cancer 2000, 83(6), 743-9.

Gasperi-Campani, et al., "Chromosomal alterations, biological features and in vitro chemosensitivity of SCLC-R1, a new cell line from human metastatic small cell lung carcinoma", European Journal of Cancer Apr. 1998, vol. 34, No. 5, 724-730.

Gerke, V. "Annexins: From Structure to Function", Physiological Reviews 2002, 82, 331-371.

Giardina, P. C. "Effect of antigen coating conditions on enzyme-linked immunosorbent assay for detection of immunoglobulin G antibody to Neisseria meningitidis serogroup Y and W135 capsular polysaccharide antigens in serum", Clin. Diagnostic Lab. Immunol. 2003, vol. 10, 1136-1140.

Gnudi, L. et al., "Adenovirus-Mediated Gene Transfer of Dominant Negative Rasasn17 in 3T3L 1 Adipocytes Does Not Alter Insulin-Stimulated PI3-Kinase Activity or Glucose Transport", Mol. Endocrinol. 1997, 11(1), 67-76.

Goydos, J. S. et al., "A Phase I Trial of a Synthetic Mucin Peptide Vaccine", J. Surgical Res. 1996, 63: 298-304.

Graham, R. A. et al., "The polymorphic epithelial mucin: potential as an immunogen for a cancer vaccine", Cancer Immunol. Immunother. 1996, 42:71-80.

Gregory, Jr, J. J. et al., "alpha-Fetoprotein and beta-Human Chorionic Gonadotropin. Their Clinical Significance as Tumour Markers", Drugs Apr. 1999, 57(4), 463-7.

(56) References Cited

OTHER PUBLICATIONS

Griffiths, B. et al., "Assignment of the polymorphic intestinal mucin gene MUC2 to chromosome-11p15", *Ann Hum Genet* 1990, 54:277-85.
Harlow, E. et al., "Antibodies: A Laboratory Manual", *Cold Spring Harbor Laboratory* 1988, 211-227.
Hsu, W. M. et al., "GRP78 expression correlates with histologic differentiation and favorable prognosis in neuroblastic tumors", *Int J Cancer* Mar. 1, 2005, 113, 920-7.
Hudelist, G. et al., "Use of high-throughput protein array for profiling of differentially expressed proteins in normal and malignant breast tissue", *Breast Cancer Res Treat.* Aug. 2004, vol. 86(3), 281-91.
Hudson, Gail A. et al., "Method for Testing Antiserum Titer and Avidity in Nephelometric Systems", *Clinical Chemistry* 1981, vol. 27, No. 11, 1838-1844.
Huhtala, M. L. et al., "Excretion of a tumor associated trypsin-inhibitor (TATI) in urine of patients with Gynecological Malignancy", *Int J Cancer* 1983, vol. 31(6), 711-714.
Ibrahim, S. O. et al., "Expression of biomarkers (p53, transforming growth factor alpha, epidermal growth factor receptor, c-erbB-2/neu and the proliferative cell nuclear antigen) in oropharyngeal squamous cell carcinomas", *Oral Oncology, Elsevier Science*, Oxford, GB May 1999, vol. 35, No. 3, 302-313.
Israeli, R. S. "Molecular Cloning of a Complementary DNA Encoding a Prostate-specific Membrane Antigen", *Cancer Res.* 1993, 53:227-30.
Jager, D. "Cancer-Testis Antigens and ING1 Tumor Suppressor Gene Product Are Breast Cancer Antigens: Characterization of Tissue-specific ING1 Transcripts and a Homologue Gene", *Cancer Res* Dec. 15, 1999, vol. 59(24), 6197-6204.
Jager, D. et al., "Identification of a tissue-specific putative transcription factor in breast tissue by serological screening of a breast cancer library", *Cancer Res* 2001, vol. 61(5), 2055-61.
Jais, et al., "Association of serum antibodies against p53 protein with poor survival in patients with Zolliger-Ellison Syndrome", *Gastroenterology* Jan. 1998, vol. 114, No. 1, 37-43.
Jalanko, et al., "Immunochemical properties of alpha-fetoprotein (AFP) and antibodies to autologous AFP", *Immunol. Commun* 1978, vol. 7, No. 2, 209-222 (Abstract only).
Janeway, et al., "Competitive Inhibition Assay for Antigen in Unknown Samples", *Immunobiology* downloaded from url www.ncbi.nlm.nih.gov/books/bv.fcgi?rid=imm.figgrp.2410, total 2 pages 2001.
Jerome, K. R. et al., "A Survivor of Breast Cancer with Immunity to MUC-1 Mucin, and Lactational Mastitis", *Cancer Immunology and Immunotherapy* Jan. 1997, Berlin, DE, vol. 43, No. 6, 355-360.
Karlan, B. Y. et al., "Peritoneal Serous Papillary Carcinoma, A Phenotypic Variant of Familial Ovarian Cancer: Implications for Ovarian Cancer Screening", *American Journal of Obstetrics & Gynecology* Apr. 1999, Mosby, St. Louis, MO, vol. 180, No. 4, 917-928.
Kasof, G. M. et al., "Livin, a novel inhibitor of apoptosis protein family", *J Biol Chem* 2001, vol. 276(5), 3238-46.
Kiefer, M. C. et al., "The CDNA and derived amino-acid sequence for human Osteopontin", *Nucleic Acids Res* 1989, 17(8), 3306.
Kim, H. et al., "Human kallikrein gene 5 (KLK5) expression is an indicator of poor prognosis in ovarian cancer", *Br. J. Cancer* 2001, vol. 84(5), 643-650.
Kirchoff, C. "A major human epididymis-specific cDNA encodes a protein with sequence homology to extracellular proteinase-inhibitors", *Biology of Reproduction* 1991, 45(2), 350-357.
Krause, P. et al., "SeroGRID: an improved method for the rapid selection of antigens with disease related immunogenicity", *J Immunol Methods* Dec. 2003, vol. 283, 261-7.
Kumar, S. et al., "Standardisation and comparison of serial dilutions and single dilution enzyme linked immunosorbent assay (ELISA) using different antigenic preparations of the Babesia (Theileria) equi parasite", *Veterinary Research* 2003, vol. 34, No. 1, 71-83.
Lindner, P. et al., "Specific Detection of His-Tagged Proteins with Recombinant Anti-His Tag scFv-Phosphatase or scFv-Phage Fusions", *Bio Techniques* 1997, 22(1), 140-149.
Lloyd, K. O. et al., "Isolation and Characterization of Ovarian Cancer Antigen CA 125 Using a New Monoclonal Antibody (VK-8) Identification As a Mucin-Type Molecule", *Int. J. Cancer* 1997, 71: 842-850.
Maeda, A. et al., "Aberrant Expression of Photoreceptor-specific Calcium-binding Protein (Recoverin) in Cancer Cell Lines", *Cancer Res.* 2000 Apr. 1, 2000, 60(7):1914-20.
Mashino, K. et al., "Expression of multiple cancer-testis antigen genes in gastrointestinal and breast carcinomas", *Br. J. Cancer* 2001, 85(5):713-720.
McIntyre, et al., "Oral contraceptive usage and the expression of CA 15-3 and C-erB-2 in the saliva of healthy women", *Oral Surg. Oral Med. Oral Pathol. Oral Radiol. Endod.* Dec. 1999, vol. 88, No. 6, 687-690.
Meichenin, M et al., "Tk, a new colon tumor-associated antigen resulting from altered O-glycosylation", *Cancer Res* Oct. 1, 2000, 60 (19), 5499-507 (Abstract only).
Microbix Biosystems Inc., "Antigen titration using the Microbix IgG ELISA", *Product Technical Bulletin*, URL://http://web.archive.org/web/2005_0526_231623/http://www.microbix.com/products/PDFs/TB-93-1AntigenTitraionousingtheMicrobixIgG+ELISA.pdf 2005.
Moll, R. et al., "The Catalog of Human Cytokeratins: Patterns of Expression in Normal Epithelia, Tumors and Cultured Cells", *Cell* Nov. 31, 1982, 31(1), 11-24.
Munemitsu, S. et al., "Regulation of intracellular beta-catenin levels by the adenomatous polyposis coli (APC) tumor-suppressor protein", *PNAS* 1995, 92:3046-50.
Munoz, et al., "New experimental criteria for optimization of solid-phase antigen concentration and stability in ELISA", *J. Immunol. Methods* 1986, 94:137-44 (Abstract only).
Muraki, et al., "Assessment of serum CYFRA 21-1 in lung cancer", *Cancer* Apr. 1996, 77(7), 1274-7.
Narod, "Genetic epidemiology of prostate cancer", *BBA—Reviews on Cancer* Jan. 1999, vol. 1423, No. 2, F1-F13.
Norum, L. F. et al., "Elevated CA 125 in Breast Cancer—A Sign of Advanced Disease", *Tumour Biol.* Jul.-Aug. 2001, 22(4), 223-8.
Pare, J. et al., "An enzyme-linked immunosorbent assay (ELISA) for serological diagnosis of *Neospora* sp. infection in cattle", *Journal of Veterinary Diagnostic Investigation* 1995, vol. 7, 352-359.
Pedrero, J. M. G. et al., "Annexin A1 Down-Regulation in Head and Neck Cancer Is Associated with Epithelial Differentiation Status", *American Journal of Pathology* 2004, 164(1), 73-79.
Perey, L. "Elevated CA125 levels in patients with metastatic breast carcinoma", *Br J Cancer* Oct. 1990, 62(4), 668-670.
Pratt, M. A. et al., "Estrogen activates raf-1 kinase and induces expression of EGR-1 in MCF-7 breast cancer cells", *Mol Cell Biochem* Dec. 1998, 189(1-2), 119-25.
Raghava, G. P. et al., "Method for determining the affinity of monoclonal antibody using non-competitive ELISA: A computer program", *Journal of Immunoassay* 1994, 15(2), 115-128.
Rao, et al., "Detection of human ovarian tumor-associated antigens by antibodies isolated from ovarian carcinoma ascitic fluid", *Am J Obstet Gynecol* Jul. 1998, vol. 159, 94-98.
Rasmussen, et al., "An ELISA for the detection of anti-neutrophil cytoplasm antibodies (ANCA)", *J. Immunol. Methods* Feb. 1990, 127(1), 139-45 (Abstract only).
Reddish, M. A. et al., "Pre-immunotherapy serum CA27.29 (MUC-1) mucin level and CD69+ lymphocytes correlate with effects of Theratope siayl-Tn-KLH cancer vaccine in active specific immunotherapy", *Cancer Immunol. Immunother* 1996, 42:303-309.
Reiter, R. E. et al., "Prostate stem cell antigen: A cell surface marker overexpressed in prostate cancer", *PNAS* 1998, 95:1735-1740.
Riddle, O. et al., "The preparation, identification and assay of prolactin—A hormone of the anterior pituitary", *Am J. Physiol* 1933, 105(1), 191-216.
Robertson, J.F. R. et al., "Assessment of Four Monoclonal Antibodies as Serum Markers in Breast Cancer", *Eur. J. Cancer* 1990, 26: 1127-1132.
Robertson, J.F. R. et al., "Prospective assessment of the role of five tumour markers in breast cancer", *Cancer Immunol. Immunother.* 1991, 33:403-410.

(56) References Cited

OTHER PUBLICATIONS

Robertson, et al., "Radioimmunohistochemistry of Epidermal Growth Factor Receptor in Breast Cancer", *Archives of Pathology and Laboratory Medicine* 2002, 126:177-81.
Rughetti, et al., "Human B-Cell Immune Response to the Polymorphic Epithelial Mucin1", *Cancer Research* Jun. 1, 1993, 53, pp. 2457-2459.
Rusciano, "Conomitant Purification of Prostatic Carcinoma Tumor Markers from Human Seminal Fluid Under Nondenaturing Conditions", *Clinical Chemistry* 1988, vol. 34, No. 12, 2528-2532.
Seabury, C. A. et al., "Evaluation of a new serum testing method for detection of prostate cancer", *J Urol* Jul. 2002, 168(1):93-9 (Abstract only).
Soussi, T. "The humoral response to the tumor-suppressor gene-product p53 in human cancer: implications for diagnosis and therapy", *Immunology Today* Aug. 1996, Elsevier Publications, Cambridge GB, vol. 17, No. 8, 354-356.
Standker, L. et al., "Isolation and characterizaton of the circulating form of human endostatin", *FEBS Lett* 1997, 420 (2-3), 129-33.
Stieber, et al., "A new marker in lung cancer", *Cancer* Aug. 1993, 72(3), 707-13.
Stiller, D et al., "Immunohistochemical demonstration of alpha-fetoprotein in testicular germ cell tumors", *Acta Histochem Suppl.* 1986, Supp-Band 33:225-31.
Szala, S. et al., "Molecular cloning of cDNA for the carcinoma-associated antigen GA733-2", *PNAS.* 1990, 87:3542-3546.
Tauchi, K. et al., "Expression of heat shock protein-70 and c-myc protein in human breast-cancer—an immunohistochemical study", *Jap J Clin Oncol* 1991, 21(4), 256-63.
Taylor-Papadimitriou, "Report on the First International Workshop on Carcinoma-Associated Mucins", *Int. J. Cancer* 1991, 49:1-5.
Thomas, W. M. et al., "Failure of CA19-9 to detect asymptomatic colorectal carcinoma", *Br. J. Cancer* 1991, 63:975-976.
Tsai, et al., "Relationship of serum alpha-fetoprotein to circulating immune complexes and complements in patients with hepatitis B surface antigen-positive hepatocellular carcinoma", *Gastroenterol Jpn* Jun. 1990, 25(3), 338-93.
Tsujimoto, Y. et al., "Analysis of the structure, transcripts, and protein products of Bcl-2, the gene involved in human follicular lymphoma", *PNAS USA* 1986, 83(14), 5214-8.
Van Milligen, Florine J. et al., "Calculation of the affinity constant KASS for solid phase antigen: A model system using monoclonal antibodies against the cat allergen Fel d I", *Journal of Immunological Methods* 1993, 162:165-173.
Von Mensdorf-Pouilly, S. "Humoral Immune Response to Polymorphic Epithelial Mucin (MUC-1) in patients with Benign and Malignant Breast Tumours", *European Journal of Cancer* 1996, vol. 32A, No. 8, 1325-1331.
Warri, A. M. et al., "Anti-oestrogen Stimulation of ERBB2 Ectodomain Shedding from BT-474 Human Breast Cells with ERBB2 Gene Amplification", *Eur. J. Cancer* 1996, 32A: 134-140.
Wolf, A. et al., "A Tumour-Associated Antigen from the Pleural Effusion of Patients with Squamous-Cell Carcinoma of Lung", *Br. J. Cancer* 1978, vol. 36, 1046-1052.
Xing, P. X. et al., "Phase I study of synthetic MUC1 peptides in breast cancer", *Int. J.Oncol.* 1995, 6(6): 1283-1289.
Yazici, H. et al., "Amplification in tumors and benign tissue of breast cancer patients", *Cancer Lett.* 1996, 107: 235-239.
Yousef, G. M. et al., "Expanded Human Tissue Kallikrein Family—A Novel Panel of Cancer Biomarkers", *Tumor Biol* 2002, 23, 185-192.
Zehentner, B. K. et al., "Mammaglobin as a Novel Breast Cancer Biomarker: Multigene Reverse Transcription-PCR Assay and Sandwich ELISA", *Clin Chem* Nov. 2004, 50(11), 2069-76.
Zehentner, B. K. et al., "Mammaglobin: A candidate diagnostic marker for breast cancer", *Clin Biochem.* Apr. 2004, 37(4), 249-57.
Zielen, et al., "Simple determination of polysaccharide specific antibodies by means of chemically modified ELISA plates", *J. Immunol. Methods* Jun. 1996, 193(1), 1-7.
"National Library of Medicine Gateway MeSH term definition downloaded from the Web", Apr. 23, 2009.
Canevari, et al., "1975-1995 Revised anti-cancer serological response: Biological significance and clinical implications", *Annals of Oncology* 1996, vol. 7, pp. 227-232.
Lubin, et al., "Analysis of p53 Antibodies in Patients with Various Cancers Define B-Cell Epitopes of Human p53: Distribution on Primary Structure and Exposure on Protein Surface", *Cancer Research* 1993, vol. 53, pp. 5872-5876.
Moingeon, "Strategies for designing vaccines eliciting Th1 responses in humans", Journal of Biotechnology 2002, vol. 98, pp. 189-198.
O'Sullivan, et al., "Polymorphic epithelial mucin from the sera of advanced breast cancer patients—isolation and partial characterisation", British Journal of Cancer 1990, vol. 61, pp. 801-808.
GB0725239.8 Search Report dated Apr. 24, 2008.
PCT/GB2008/004260 International Search Report and Written Opinion, mailed Feb. 27, 2009.
Chapman, C. J. et al., "Autoantibodies in lung cancer: possibilities for early detection and subsequent cure", *Thorax* Sep. 26, 2007, 0:1-6. doi:10.1136/thx.2007.083592.
He, Ping et al., "Proteomics-based identification of alpha-enolase as a tumor antigen in non-small lung cancer", *Cancer Sci* Aug. 2007, 98(8), 1234-1240.
Lidner, et al., "Specific Detection of His-Tagged Proteins with Recombinant Anti-His Tag scFv-Phosphatase or scFv-Phage Fusions", *Biotechniques* 1997, vol. 22, 140-149.
Petrarca, et al., "Human Antibodies Against the Polymorphic Epithelial Mucin in Ovarian Cancer Patients Recognise a Novel Sequence in the Tandem Repeat Region", *European Journal of Cancer* 1996, vol. 32A, 2155-2163 (Abstract only).
Schjetlein, Rune et al., "Choice of Standard Plasma for Diagnosis and Quantitation of Lupus Anticoagulants", *Thrombosis Research* 1993, 72:287-294.
Yamadori, et al., "A case of non-specific interstitial pneumonia associated with primary lung cancer: possible role of antibodies to lung cancer cells in the pathogenesis of non-specific interstitial pneumonia", *Respiratory Medicine* 1999, 93, 754-756.
Butler, W. T. et al., "Osteopontin—Structure and biological activity", *CIBA Foundation Symposia* 1988, 136, 203-206.
Zhu, Liyin et al., "Adenocarcinoma of Duodenum and Ampoulla of Vater: Clinicopathology Study and Expression of p53, c-neu, TGF-a, CEA, and EMA", Journal of Surgical Oncology 1996, vol. 61; 100-105.
Bellone et al., "Cancer Immunotherapy: Synthetic and Natural Peptides in the Balance", Immunology Today, Oct. 1999, vol. 20, No. 10, pp. 457-462.
Ben-Efraim, "One Hundred Years of Cancer Immunotherapy: A Critical Appraisal", Tumor Biology, 1999, vol. 20, pp. 1-24.
Byers, "What Can Radomized Controled Trials Tell Us About Nutrition and Cancer Prevention?", CA Cancer J. Clinical, vol. 49, No. 6, Nov./Dec. 1999.
Coomber, et al., "Characterisation and Clinicopathological Correlates of Serum Anti-p53 Antibodies in Breast and Colon cancers", J Cancer Res Clin Oncol, 1996, vol. 122, No. 12, pp. 757-762.
Frazier, "Is Vaccine Therapy the Future in Cancer Prevention?", Expert Opinion., Pharmacother., 2004, vol. 5, No. 12, pp. 2427-2434.
Granziero et al., "Adoptive Immunotherapy Prevents Prostate Cancer in a Transgenic Animal Mode", Eur. J. Immunol., 1999, vol. 29. pp. 1127-1138.
Hirasawa, et al., "Natural Autoantibody to MUC1 Is a Prognostic indicator for Non-Small Cell Lung Cancers", Am J Respir Crit Care Med, 2000, vol. 161, pp. 589-594.
U.S. Appl. No. 12/343,047, "Office Action" dated Apr. 5, 2012, 18.
U.S. Appl. No. 12/343,047, "Office Action", Nov. 26, 2012.
Harlow et al., "Antibodies: A Laboratory Manual", Cold Spring Harbor Laboratory, 1988, 562-563.
Non-Final Office Action dated May 23, 2013 in U.S. Appl. No. 11/814,516, 9 pages.
Notice of Allowance dated May 30, 2013 in U.S. Appl. No. 11/854,050, 6 pages.
Final Office Action dated Jun. 5, 2013 in U.S. Appl. No. 12/343,047, 24 pages.

(56) References Cited

OTHER PUBLICATIONS

Hirasawa et al., "KL-6, a human MUC1 mucin, is chemotactic for human fibroblasts.", American Journal of Respiratory Cell and Molecular Biology [1997, 17(4):501-507].

Sakurai et al., "Differential expression of the glycosylated forms of MUC1 during lung development", European Journal of Histochemistry 2007, vol. 51 issue 2 (Apr.-Jun.); 95-102.

Lenner et al., "Serume antibodies against p53 in relation to cancer risk and prognosis in breast cancer: a population-based epidemiological study", British Journal of Cancer, Feb. 1999, vol. 79, pp. 927-932.

Regidor et al., "Detection of p53 auto-antibodies in the aera of breast cancer patients with a new recurrence using an ELISA assay. Does a correlation with the recurrence free interval exist?", European Journal of Gynaecological Oncology, 1996, vol. 17, No. 3, pp. 192-199.

Vennegoor et al., "Autoantibodies to p53 in ovarian cancer patients and healthy women: a comparison between whole p53 protein and 18-mer peptides for screening purposes", Cancer Letters, 1997, vol. 116, pp. 93-101.

* cited by examiner

FIG. 1. Post Ig disruption gel filtration chromatogram.

Silver stained gel, c-myc purification, post immunoaffinity

1 – major c-myc peak, room temp purification
2 – major c-myc peak, 4°C purification
3 – minor c-myc peak, room temp purification
4 – minor c-myc peak, 4°C purification Reactivity of human anti-MUC1 antibodies purified against cancer associated MUC1 from seroma.

Pt-nMUC1 – urinary MUC1 from patient M, 2 years prior to cancer diagnosis.
Pt-MUC1 – MUC1 derived from the seroma of patient M, after diagnosis with cancer.
BSA-AG – bovine serum albumen conjugated to MUC1 protein core peptide.

Titration of PE MUC1

TUMOUR MARKER PROTEINS AND USES THEREOF

CROSS REFERENCE TO RELATED APPLICATIONS

This application is the U.S. national phase of International Application No. PCT/GB2003/004950 filed on Nov. 13, 2003 and published in English on May 27, 2004 as International Publication No. WO 2004/044950, which application claims priority to GB Patent Application No. 0226622.9 filed on Nov. 14, 2002, the contents of which are incorporated by reference herein.

FIELD OF THE INVENTION

The invention relates to tumour marker proteins and their preparation from fluids from one or more cancer patients, wherein said fluids are those which collect in a body cavity or space which is naturally occurring or which is the result of cancer or medical intervention for cancer. Exemplary fluids are ascites, pleural effusion, seroma, hydrocoele and wound drainage fluid. The invention also relates to preparation of tumour marker proteins from excretions taken from patients with cancer.

The said tumour marker proteins are useful in cancer detection methods which involve detecting or quantitatively measuring autoantibodies to circulating tumour markers or markers expressed on or in tumour cells and in various research applications. The invention is also directed to such uses.

BACKGROUND TO THE INVENTION

The development and progression of cancer in a patient is generally found to be associated with the presence of markers in the bodily fluid of the patient, these "tumour markers" reflecting different aspects of the biology of the cancer (see Fateh-Maghadam, A. & Steilber, P. (1993) Sensible use of tumour markers. Published by Verlag GMBH, ISBN 3-926725-07-9). Tumour markers are often found to be altered forms of wild-type proteins expressed by "normal" cells, in which case the alteration may be a change in primary amino acid sequence, a change in secondary, tertiary or quaternary structure or a change in post-translational modification, for example, abnormal glycosylation. In addition, wild-type proteins which are up-regulated or over-expressed in tumour cells, possibly as a result of gene amplification or abnormal transcriptional regulation, may also be tumour markers.

Established assays for tumour markers present in bodily fluids tend to focus on the detection of tumour markers which reflect tumour bulk and as such are of value late in the disease process, for example in the diagnosis of metastatic disease. The most widely used of these markers include carcinoembryonic antigen (CEA) and the glycoprotein termed CA 15.3, both of which have been useful mainly as indicators of systemic disease burden and of relapse following therapy (Molina, R., Zanon, G., Filella, X. et al. Use of serial carcinoembryonic antigen and CA 15.3 assays in detecting relapses in breast cancer patients. (1995) *Breast Cancer Res Treat* 36: 41-48). These markers are of limited use earlier in the course of the disease, for example in early detection or in the screening of asymptomatic patients. Thus, in the search for tumour markers present in bodily fluid that are of use in assisting diagnosis earlier in the disease process the present inventors have sought to identify markers which do not depend on tumour bulk per se.

Differences between a wild type protein expressed by "normal" cells and a corresponding tumour marker protein may, in some instances, lead to the tumour marker protein being recognised by an individual's immune system as "non-self" and thus eliciting an immune response in that individual. This may be a humoral (i.e B cell-mediated) immune response leading to the production of autoantibodies immunologically specific to the tumour marker protein. Autoantibodies are naturally occurring antibodies directed to an antigen which an individual's immune system recognises as foreign even though that antigen actually originated in the individual. They may be present in the circulation as circulating free autoantibodies or in the form of circulating immune complexes consisting of autoantibodies bound to their target tumour marker protein.

As an alternative to the direct measurement or detection of tumour marker protein in bodily fluids, assays may be developed to measure the immune response of the individual to the presence of tumour marker protein in terms of autoantibody production. Such assays essentially constitute indirect detection of the presence of tumour marker protein. Because of the nature of the immune response, it is likely that autoantibodies can be elicited by a very small amount of circulating tumour marker protein and indirect methods which rely on detecting the immune response to tumour markers will consequently be more sensitive than methods for the direct measurement of tumour markers in bodily fluids. Assay methods based on the detection of autoantibodies may therefore be of particular value early in the disease process and possibly also in relation to screening of asymptomatic patients, for example in screening to identify individuals "at risk" of developing disease amongst a population of asymptomatic individuals. Furthermore, they may be useful for earlier detection of recurrent disease.

Tumour marker proteins observed to elicit serum autoantibodies include a particular class of mutant p53 protein, described in U.S. Pat. No. 5,652,115, which can be defined by its ability to bind to the 70 kd heat shock protein (hsp70). p53 autoantibodies can be detected in patients with a number of different benign and malignant conditions (described in U.S. Pat. No. 5,652,115) but are in each case present in only a subset of patients. For example, one study utilizing an ELISA assay for detection of autoantibodies directed against the p53 protein in the serum of breast cancer patients reported that p53 autoantibodies were produced by 26% of patients and 1.3% of control subjects (Mudenda, B., Green, J. A., Green, B. et al. The relationship between serum p53 autoantibodies and characteristics of human breast cancer, (1994) *Br J Cancer* 69: 4445-4449). A second tumour marker protein known to elicit serum autoantibodies is the epithelial mucin MUC1 (Hinoda, Y. et al. (1993) *Immunol Lett*. 35: 163-168; Kotera, Y. et al. (1994) *Cancer Res*. 54: 2856-2860).

WO 99/58978 describes methods for use in the detection/diagnosis of cancer which are based on evaluating the immune response of an individual to two or more distinct tumour markers. These methods generally involve contacting a sample of bodily fluid taken from the individual with a panel of two or more distinct tumour marker antigens, each derived from a separate tumour marker protein, and detecting the formation of complexes of the tumour marker antigens bound to circulating autoantibodies immunologically specific for the tumour marker proteins. The presence of such circulating autoantibodies is taken as an indication of the presence of cancer.

Cancer detection methods based on detection of circulating autoantibodies are frequently immunoassays utilizing an "immunoassay reagent" reactive with the circulating autoantibodies. Typically, the "reagents" used in such assays comprise recombinant tumour marker proteins (expressed in bacterial, insect, yeast or mammalian cells) or chemically synthesised tumour marker antigens, which may comprise substantially whole tumour marker proteins, or fragments thereof, such as short peptide antigens. Other potential sources of tumour-associated proteins for use as the basis of immunoassay reagents for the detection of anti-tumour autoantibodies include cultured tumour cells (and the spent media used for their growth), tumour tissue, and serum from individuals with neoplasia. The majority of these sources have significant drawbacks, as discussed below.

With cultured tumour cells (and their spent media) the amount of expressed protein can vary depending on growth phase at the time of harvest, leading to variations in quality and quantity. In addition, the desired protein is generally present at low concentration, therefore it is time-consuming to purify sufficient quantities of protein. Furthermore, the cell stock will be clonal, unlike cell stock in a tumour which is likely to have become heterogeneous in nature during the growth of the neoplasm, therefore producing variations in protein (especially in the degree of glycosylation).

Recombinant proteins expressed in bacterial cells are not glycosylated, and thus significantly different from naturally glycosylated proteins. In addition, refolding of recombinantly expressed proteins may not be appropriate, thus giving an incorrect conformation for auto-antibody recognition.

Tumour tissue is usually only available in small quantities and the purification of proteins therefrom is laborious and time consuming.

Serum samples are usually available only in small quantities, therefore it is difficult to purify sufficient quantities of protein.

The present inventors have now determined that significant advantages can be gained by the use of tumour marker antigens purified from bodily fluids derived from a body cavity or space in which a tumour is present or with which it is or was associated, such as ascites fluid, pleural effusion, seroma, hydrocoele or wound drainage fluid, or from excretions, as the "reagent" in auto-antibody immunoassays. In particular, the inventors have observed that use of reagents comprising tumour marker antigens purified from bodily fluids derived from the above defined body cavities or spaces results in increased sensitivity (as compared to the use of reagents derived from a "normal" body fluid) and produces a more "clinically relevant" result. There are also significant practical advantages to be gained from the use of such fluids as a source of assay reagent.

SUMMARY OF THE INVENTION

In a first aspect the invention relates to a method of detecting cancer-associated anti-tumour autoantibodies, which method is an immunoassay comprising contacting a sample to be tested for the presence of such autoantibodies with an immunoassay reagent and detecting the presence of complexes formed by specific binding of the immunoassay reagent to any cancer-associated anti-tumour autoantibodies present in the sample, wherein the immunoassay reagent comprises tumour marker protein prepared from bodily fluid derived from a body cavity or space within which a tumour is or was present or with which a tumour is or was associated, from one or more cancer patients and/or tumour marker protein prepared from an excretion from one or more cancer patients, wherein said tumour marker protein exhibits selective reactivity with cancer-associated anti-tumour autoantibodies.

In a second aspect the invention relates to use of tumour marker protein prepared from bodily fluid derived from a body cavity or space within which a tumour is or was present or with which a tumour is or was associated, of one or more cancer patients and/or tumour marker protein derived from an excretion of one or more cancer patients in the manufacture of an immunoassay reagent exhibiting selective reactivity with cancer-associated anti-tumour autoantibodies.

In a third aspect, the invention relates to a method of preparing a tumour marker protein which method comprises isolating said tumour marker protein from bodily fluid wherein said fluid is:

(i) collected from a body cavity or space in which a tumour is or was present or with which a tumour is or was associated, and (ii) said fluid represents the pooled fluid samples from two or more cancer patients.

In a fourth aspect, the invention relates to a method of preparing a tumour marker protein which method comprises isolating said tumour marker protein from an excretion wherein:

(i) said excretion or any component thereof has been in contact with a tumour or tumour cells, and (ii) said excretion represents pooled excretion samples from two or more cancer patients.

In a fifth aspect the invention relates to tumour marker protein preparations prepared using the methods described above which are substantially immunoglobulin free and to kits and reagents comprising said preparations.

DETAILED DESCRIPTION OF THE INVENTION

In the first aspect, the invention relates to a method of detecting "cancer-associated" anti-tumour autoantibodies.

The term "cancer-associated" anti-tumour autoantibodies refers to autoantibodies which are characteristic of the cancer disease state, and which are directed against epitopes present on forms of tumour marker proteins which are preferentially expressed in the cancer disease state.

The method of the invention comprises an immunoassay to detect and/or quantitatively measure autoantibodies immunologically specific for one or more tumour marker proteins, and is characterised in that the "immunoassay reagent" used in the immunoassay comprises tumour marker protein prepared from bodily fluid derived from a body cavity or space in which a tumour is or was present or with which a tumour is or was associated, from one or more cancer patients and/or tumour marker protein prepared from an excretion of one or more cancer patients. Generally, the excretion will have passed through an organ in which cancer is present wherein the excretion is in contact with said cancer, or the excretion will include one or more components which have been in contact with cancer elsewhere in the body. A particular example is bile which may be in contact with cancer in the gall bladder but will appear in the faeces.

The immunoassay reagent exhibits "selective reactivity" with cancer-associated anti-tumour autoantibodies. As used herein "selective reactivity" means a tumour marker protein has a greater affinity for autoantibodies to the tumour-associated antigen than it does for any antibody or autoantibody made to the same antigen which exists in the normal i.e. non-tumour possessing state.

The term "body cavity or space" includes any body cavity or space, whether it be a natural cavity or a space or cavity arising as a result of diseases or medical intervention including collapsed or former cavities. The fluid is derived from such a cavity or space in which a tumour is or was present or with which a tumour is or was associated. Preferably the "bodily fluid derived from a body cavity" will be a tumour-induced body fluid, meaning a body fluid which is produced during the disease process, for example in response to or as a consequence of the presence of tumour cells. Exemplary body fluids are ascites, pleural effusion, seroma, hydrocoele and wound drainage fluid.

For the avoidance of doubt "bodily fluids derived from a body cavity or space" do not include fluids derived from the systemic circulation, such as whole blood or serum.

The term "excretion" includes, inter alia, urine, faeces, and seminal fluid.

The general features of immunoassays, for example ELISA, radioimmunoassays and the like, are well known to those skilled in the art (see Immunoassay, E. Diamandis and T. Christopoulus, Academic Press, Inc., San Diego, Calif., 1996). Immunoassays for the detection of antibodies having a particular immunological specificity (e.g. autoantibodies having immunological reactivity with a given tumour marker protein) generally require the use of a reagent that exhibits specific immunological reactivity with the antibody under test. Depending on the format of the assay this reagent may be immobilised on a solid support. A sample to be tested for the presence of the antibody is brought into contact with the reagent and if antibodies of the required immunological reactivity are present in the sample they will immunologically react with the reagent to form autoantibody-reagent complexes which may then be detected or quantitatively measured.

Suitable samples of tumour marker protein for use as the basis of the "immunoassay reagent" may be isolated from bodily fluids derived from a body cavity or space from one or more cancer patients and/or from excretions from one or more cancer patients using standard protein purification techniques, such as are generally known in the art. For example, tumour marker proteins may be isolated by affinity chromatography using a suitable antibody (or antibody fragment) immunologically specific for the tumour marker protein. The inventors have shown in the accompanying examples that several different tumour marker proteins may be purified using purification methods based on affinity chromatography. It would be apparent to the skilled reader that analogous purification methods used for any other tumour marker proteins, with the use of a suitable antibody or antibody fragment.

The starting material of bodily fluids derived from a body cavity and/or excretions is/are taken from one or more cancer patients. In this context the term "cancer patient" includes an individual previously diagnosed as having cancer. The fluid/excretion may be taken from a single patient or samples from two or more patients may be pooled together. Samples may be pooled from two or more patients having the same or different stages of the same or different types of cancers. Samples may also be pooled from different types of bodily fluids or excretions from a single or multiple patients. Advantageously, an immunoassay reagent prepared from fluid and/or excretion taken from cancer patient(s) with a particular type of cancer may be used to assist in the diagnosis of the same types of cancers in the other individuals.

In one embodiment the "cancer patient" from which the fluid/excretion is taken may be the same patient which it is later intended to test using the assay reagent. For example, a stock of reagent prepared from a patient diagnosed with cancer may be used at a later date to assess the immune status of the same patient, for example to monitor disease progression and/or to assess the effectiveness of a course of anti-cancer treatment in that patient.

The "immunoassay reagent" or "tumour marker preparation" may comprise substantially whole tumour marker protein, for example tumour marker protein substantially in the form in which it is isolated from the fluid/excretion, or it may comprise a fragment of the tumour marker protein. To be effective as an immunoassay reagent any such "fragment" must retain immunological reactivity with the (auto)antibodies for which it is desired to test using the reagent. Suitable fragments might, for example, be prepared by chemical or enzymatic cleavage of the isolated tumour marker protein.

Depending on the precise nature of the immunoassay in which it will be used, the "reagent" or "tumour marker protein preparation" may comprise a tumour marker protein, or fragment thereof, linked to one or more further molecules which impart some desirable characteristic not naturally present in the tumour marker protein. For example, the tumour marker protein may be conjugated to a revealing label, such as a fluorescent label, coloured label, luminescent label, radiolabel or heavy metal such as colloidal gold.

The tumour marker protein as prepared by the method described herein can also be immobilized for use on a solid support such as a bead or surface of a well of a multiwell plate. The immobilization may be by absorption or by covalent attachment.

The tumour marker protein (or assay reagent comprising such protein) is preferably substantially immunoglobulin free by virtue of the fact that following isolation, for example, by affinity chromatography, the protein preparation is treated to specifically remove contaminating immunoglobulins.

The use of an immunoassay reagent comprising a tumour marker protein (or fragment thereof) isolated from body cavity fluids and/or excretions taken from one or more cancer patients provides significant advantages over the use of other reagents, such as recombinantly expressed or chemically synthesised polypeptides, in the clinical detection of cancer (including diagnosis, monitoring of disease recurrence or disease progression, etc).

It might be expected that the precise characteristics of tumour marker proteins isolated from cancer patients could vary depending upon the source material (e.g. tissue or fluid) from which the tumour marker protein is isolated. For example, the characteristics of proteins isolated from urine may be different to those isolated from whole blood or serum, which may be different again to those isolated from ascites or pleural effusion. This may in turn affect the utility of the tumour marker protein as an assay reagent.

In fact, the inventors have surprisingly observed that reagents prepared from tumour marker proteins isolated from body cavity-derived fluids or excretions from cancer patients, particularly ascites fluid, pleural effusion, seroma or wound drainage fluid are generally more specific for cancer-associated autoantibodies than reagents based on the equivalent proteins isolated from "normal" individuals. This increased specificity for cancer-associated autoantibodies means that immunoassays based on the use of reagents prepared from body cavity-derived fluids or excretions from cancer patients produce results that are more "clinically relevant" in the detection of an immune response to cancer.

Prior to the present invention, it was not clear how reagents comprising antigens prepared from body cavity-derived fluids or excretions from cancer patients would perform as reagents for immunological detection of autoantibodies. In particular, it was not known whether such antigens would exhibit higher specificity for cancer-associated autoantibodies. It could not be predicted whether antigens from such sources would perform similarly to or better than antigen prepared from blood or serum, in terms of their ability to detect cancer-associated autoantibodies. Whilst it was known that tumour marker proteins may be present in fluids derived from body cavities and spaces, there is generally more potential for the antigens in these body cavities and spaces to be broken down. This in turn would mean that they might not detect autoantibodies as well as serum-derived antigens. Furthermore, it could not be concluded with certainty that antigens derived from cavity-derived fluids and excretions are immunologically similar to antigens derived from serum. Accordingly, it was surprising to observe that antigens prepared from cavity-derived fluids and excretions of cancer patients perform well as immunoassay reagents.

The inventors postulate that the improved specificity observed with the use of reagents prepared from fluids derived from body cavities of cancer patients, such as ascites, pleural effusion, seroma or wound drainage fluid, is due to the origin of such fluids within the body cavities or spaces of cancer patients. It is postulated that fluids originating in body cavities or spaces due to the presence of a tumour in contact with the major organs may pick up more "cancer-associated" forms of the tumour marker protein, which are actually relevant to the cancer disease state, and contain less of the corresponding "normal" proteins. Since it is generally differences between "tumour" marker proteins and their "normal" counterparts which trigger the development of an immune response (i.e. autoantibody production), the inventors hypothesise that reagents based on the use of tumour markers isolated from cancer patients will be more specific for cancer autoantibodies than the equivalent "normal" proteins. This is indeed the case with tumour marker antigens isolated from ascites, pleural effusion or seroma, as shown in the accompanying Examples.

There are further practical advantages associated with the use of ascites fluid, pleural effusion, seroma, hydrocoele or wound drainage fluid, as a source of tumour marker proteins. These fluids may be readily removed from patients in relatively large volumes as part of the therapeutic strategy. This material, which would otherwise be discarded, is a valuable source of useful assay reagent.

Given that fluids such as ascites fluid, pleural effusion, seroma, hydrocoele or wound drainage fluid are produced in large volumes, there was doubt as to whether the concentration of tumour marker proteins in such fluids would be high enough to enable such fluids to be used as a practical source of antigens. One might reasonably expect the concentration of tumour marker proteins to be more dilute in such fluids as compared to blood or serum. Surprisingly, the inventors observed that the concentrations of tumour marker proteins in such fluids are in fact significantly higher than in serum. Accordingly, there are substantial benefits to be gained in terms of yield in recovering tumour marker proteins from such fluids.

Furthermore, it has also been observed by the inventors that additional significant advantages can be secured by pooling body cavity fluid samples or excretions from two or more patients. Apart from increasing protein yield, the product secures at least as good a detection rate as marker protein from an individual sample while, at the same time, being more consistent in its characteristics from batch to batch. Thus, adequate affinity of the antigen can be relied upon every time.

In particular embodiments the methods of the invention may comprise immunoassays to (simultaneously) detect two or more types of autoantibodies, each having specificity for different tumour marker proteins or for different epitopes on the same tumour marker proteins. These methods will typically involve use of a panel of two or more assay reagents, each reagent comprising a different tumour marker protein. These methods, which may be hereinafter referred to as "panel assays", utilise a panel of two or more reagents to monitor the overall immune response of an individual to a tumour or other carcinogenic/neoplastic change. These methods thus detect a "profile" of the immune response in a given individual, indicating which tumour markers elicit an immune response resulting in autoantibody production. The use of a panel of two or more reagents to monitor production of autoantibodies against two or more different tumour markers is generally more sensitive than the detection of autoantibodies to single markers and gives a much lower frequency of false negative results.

The methods of the invention are preferred for the detection of circulating free autoantibodies, but may be adapted for detection of autoantibodies present in immune complexes, as would be appreciated by the skilled reader, for example by the competitive use of labelled tumour marker.

In preferred applications the method of the invention will be used to detect the presence of cancer-associated anti-tumour autoantibodies in human subjects or patients, and will most preferably take the form of an in vitro immunoassay, performed on samples of bodily fluid taken from the subject/patient. Such in vitro immunoassays are non-invasive and can be repeated as often as is thought necessary to build up a profile of autoantibody production in a patient, either prior to the onset of disease, as in the screening of "at risk" individuals, or throughout the course of disease (further discussed below in relation to preferred applications of the method). As used herein the term "bodily fluid", when referring to the material to be tested for the presence of autoantibodies by immunoassay, includes inter alia plasma, serum, whole blood, urine, sweat, lymph, faeces, cerebrospinal fluid, ascites, pleural effusion, seminal fluid, sputum or nipple aspirate. The type of bodily fluid used may vary depending upon the type of cancer involved and the clinical situation in which the assay is used. In general, it is preferred to perform the assays on samples of serum or plasma.

As aforesaid, the "immunoassay" used to detect/quantitate cancer-associated autoantibodies may be carried out according to standard techniques known in the art. In a most preferred embodiment the immunoassay may be an ELISA. ELISAs are generally well known in the art. In a typical "sandwich" ELISA a reagent having specificity for the autoantibodies under test is immobilised on a solid surface (e.g. the wells of a standard microtiter assay plate, or the surface of a microbead) and a sample of body fluid to be tested for the presence of autoantibodies is brought into contact with the immobilised reagent. Any autoantibodies of the desired specificity present in the sample will bind to the immobilised reagent. The bound autoantibody/reagent complexes may then be detected using any suitable method. In one preferred embodiment a labelled secondary anti-human immunoglobulin antibody, which specifically recognises an epitope common to one or more classes of human immunoglobulins, is used to detect the autoantibody/reagent complexes. Typically the secondary antibody will be anti-IgG or anti-IgM. The secondary antibody is usually labelled with a detectable marker, typically an enzyme marker such as, for example, peroxidase or alkaline phosphatase, allowing quantitative detection by the addition of a substrate for the enzyme which generates a detectable product, for example a coloured, chemiluminescent or fluorescent product. Other types of detectable labels known in the art may be used with equivalent effect.

ELISA's may be performed in a qualitative format, in which the objective is merely to determine the presence or absence of autoantibodies in the sample, or in a quantitative format, which provides a measurement of the quantity of autoantibodies present in the sample. For quantitative assays, a standard curve may be generated by measuring the signal obtained (using the same detection reaction as will be used for the assay) from a series of standard samples containing known concentrations of antibodies having similar specificity as the autoantibodies under test. The quantity of autoantibodies present in the sample under test may then be interpolated from the standard curve.

Panel assays may be performed in a multi-well format in which each one of the two or more assay reagents is placed in a separate well of a multi-well assay plate or, alternatively, in a single-pot format in which the two or more assay reagents are placed in a single container.

The method of the invention may be adapted for use in the detection of autoantibodies to essentially any tumour marker protein for which a suitable "assay reagent" may be prepared from bodily fluid derived from a body cavity and/or from an excretion from a cancer patient. In particular, the method may be adapted to detect/measure autoantibodies to the epidermal growth factor receptor-related protein c-erbB2 (Dsouza, B. et al. (1993) *Oncogene*. 8: 1797-1806), the glycoprotein MUC1 (Batra, S. K. et al. (1992) *Int. J. Pancreatology*. 12: 271-283) and the signal transduction/cell cycle regulatory proteins Myc (Blackwood, E. M. et al. (1994) *Molecular Biology of the Cell* 5: 597-609), p53 (Matlashewski, G. et al. (1984) *EMBO J.* 3: 3257-3262; Wolf, D. et al. (1985) *Mol. Cell. Biol.* 5: 1887-1893) and ras (or Ras) (Capella, G. et al. (1991) *Environ Health Perspectives*. 93: 125-131), and also BRCA1 (Scully, R. et al. (1997) *PNAS* 94: 5605-10), BRCA2 (Sharan, S. K. et al. (1997) *Nature*. 386: 804-810), APC (Su, L. K. et al. (1993) *Cancer Res*. 53: 2728-2731; Munemitsu, S. et al. (1995) *PNAS* 92: 3046-50), CA125 (Nouwen, E. J. et al. (1990) *Differentiation*. 45: 192-8), PSA (Rosenberg, R. S. et al. (1998) *Biochem Biophys Res Commun*. 248: 935-939), carcinoembryonic antigen CEA (Duffy, M. J. (2001) *Clin Chem, April* 47(4):624-30), and CA19.9 (Haga, Y. et al (1989) *Clin Biochem* (1989) October 22(5): 363-8). However, the invention is not intended to be limited to the detection of autoantibodies to these particular tumour markers.

The assay method of the invention may be employed in a variety of different clinical situations. In particular, the method may be used in the detection or diagnosis of cancer, in monitoring the progress of cancer or other neoplastic disease in a patient, in detecting early neoplastic or early carcinogenic change in an asymptomatic human subject, in screening a population of asymptomatic human subjects in order to identify those subjects who are at increased risk of developing cancer, in monitoring the response of a cancer patient to anti-cancer treatment, in the detection of recurrent disease in a patient previously diagnosed as having cancer who has undergone anti-cancer treatment to reduce the amount of cancer present, or in the selection of an anti-cancer vaccine for use in a particular patient.

The inventors have generally observed that levels of cancer-associated autoantibodies show a positive correlation with disease state (see also WO 99/58979, the contents of which are incorporated herein by reference). Hence, when the method of the invention is used in clinical applications increased levels of anti-tumour marker autoantibodies, as compared to suitable controls, are generally taken as an indication of the cancer disease state.

For example, when the immunoassays are used in the diagnosis of cancer, the presence of an elevated level of autoantibodies, as compared to "normal" control individuals, is taken as an indication that the individual has cancer. The "normal" control individuals will preferably be age-matched controls not having any diagnosis of cancer based on clinical, imaging and/or biochemical criteria.

When the immunoassays are used in monitoring the progress of cancer or other neoplastic disease in a patient, the presence of an elevated level of autoantibodies, as compared to a "normal control", is taken as an indication of the presence of cancer in the patient. The "normal control" may be levels of autoantibodies present in control individuals, preferably age-matched, not having any diagnosis of cancer based on clinical, imaging and/or biochemical criteria. Alternatively, the "normal control" may be a "base-line" level established for the particular patient under test. The "base-line" level may be, for example, the level of autoantibodies present when either a first diagnosis of cancer or a diagnosis of recurrent cancer was made. Any increase above the base-line level would be taken as an indication that the amount of cancer present in the patient has increased, whereas any decrease below the base-line would be taken as an indication that the amount of cancer present in the patient has decreased. The "base-line" value may also be, for example, the level before a new treatment is commenced. A change in the level of autoantibodies would be taken as an indication of the effectiveness of the therapy. The direction of the "change" (i.e. increase vs decrease) indicating a positive response to treatment will be dependent upon the precise nature of the treatment. For any given treatment the direction of the "change" in antibody levels indicating a positive result may be readily determined, for example by monitoring autoantibody levels in comparison to other clinical or biochemical indicators of response to the treatment.

When the immunoassays are used in screening a population of asymptomatic human subjects to identify those subjects who are at increased risk of developing cancer, individuals having an elevated level of autoantibodies, as compared to "normal" control individuals, are identified as being "at risk" of developing cancer. The "normal" control individuals will preferably be age-matched controls not identified as having any predisposition to developing cancer or any significant elevated risk of developing cancer. An exception to this may be where age itself is a major risk factor.

When the immunoassays are used in monitoring the response of a cancer patient to anti-cancer treatment, the presence of a decreased level of autoantibodies after treatment is taken as an indication that the patient has responded positively to the treatment. A base-line level of autoantibodies taken before treatment is commenced may be used for comparison purposes in order to determine whether treatment results in a "decrease" in autoantibody levels.

When the immunoassays are used in detection of recurrent disease, the presence of an increased level of autoantibodies in the patient, as compared to a "normal control", is taken as an indication that disease has recurred. The "normal control" may be levels of autoantibodies present in control individuals, preferably age-matched not having any diagnosis of cancer based on clinical, imaging and/or biochemical criteria. Alternatively, the "normal control" may be a "base-line" level established for the particular patient under test. The "base-line" level may be, for example, the level of autoantibodies present during a period of remission from disease based on clinical, imaging and/or biochemical criteria.

The assay method of the invention may be applied in the detection of many different types of cancer, of which examples are breast, bladder, colorectal, prostate and ovarian cancers. The assays may complement existing methods of screening and surveillance. For example, in the case of primary breast cancer immunoassays for autoantibodies could be used to alert clinicians to biopsy small lesions on mammograms which radiographically do not appear suspicious or to carry out breast imaging or to repeat imaging earlier than planned. In the clinic, the assay methods of the invention are expected to be more objective and reproducible compared to current imaging techniques (i.e. mammography and ultrasound), the success of which can be operator-dependent.

"Panel assays" may be tailored having regard to the particular clinical application. A panel of reagents for detection of autoantibodies to at least p53 and c-erbB2 is particularly useful for many types of cancer and can optionally be supplemented with other markers having a known association with the particular cancer, or a stage of the particular cancer, to be detected. For example for breast cancer the panel might include MUC 1 and/or c-myc and/or BRCA1 and/or BRCA2 and/or PSA whereas bladder cancer the panel might optionally include MUC 1 and/or c-myc, for colorectal cancer ras and/or APC, for prostate cancer PSA and/or BRCA 1 and/or BRCA2 or for ovarian cancer BRCA1 and/or BRCA2 and/or CA125. There are other preferred embodiments in which p53 or c-erbB2 are not necessarily essential. For example, in the case of breast cancer suitable panels could be selected from the following:

p53 and MUC 1 with optional c-erbB2 and/or c-myc, and/or BRCA1 and/or BRCA2 and/or PSA;
p53 and c-myc with optional c-erbB2 and/or MUC1 and/or BRCA1 and/or BRCA2 and/or PSA;
p53 and BRCA1 with optional c-erB2 and/or MUC 1 and/or c-myc and/or BRCA2 and/or PSA;
p53 and BRCA2 with optional c-erbB2 and/or MUC 1 and/or c-myc and/or BRCA1 and/or PSA;
c-erbB2 and MUC 1 with optional p53 and/or c-myc, and/or BRCA1 and/or BRCA2 and/or PSA;
c-erbB2 and c-myc with optional p53 and/or MUC1 and/or BRCA1 and/or BRCA2 and/or PSA;
c-erbB2 and BRCA1 with optional p53 and/or MUC 1 and/or c-myc and/or BRCA2 and/or PSA;
c-erbB2 and BRCA2 with optional p53 and/or MUC 1 and/or c-myc and/or BRCA1 and/or PSA.

In the case of colorectal cancer suitable panels could be selected for example from the following:
p53 and ras with optional c-erbB2 and/or APC;
p53 and APC with optional c-erbB2 and/or Ras;
Ras and APC with optional p53 and/or c-erbB2
Such panels might also include CEA or CA19-9.

In the case of prostate cancer suitable panels could be selected for example from the following:
p53 and PSA with optional BRCA1 and/or BRCA2 and/or c-erbB2;
c-erbB2 and PSA with optional p53 and/or BRCA1 and/or BRCA2.

In the case of ovarian cancer suitable panels could be selected for example from the following:
p53 and CA125 with optional c-erbB2 and/or BRCA1 and/or BRCA2;
c-erbB2 and CA125 with optional p53 and/or BRCA1 and/or BRCA2.

In a further embodiment, the immunoassay method of the invention may be used in the selection of an anti-cancer vaccine for use in a particular patient. In this embodiment a sample of bodily fluid taken from the patient is tested using a panel of two or more immunoassay reagents, each corresponding to a different tumour marker protein, in order to determine the relative strength of the patient's immune response to each of the different tumour marker proteins. The "strength of immune response" to a given tumour marker protein or proteins is indicated by the presence and/or the amount of cancer-associated autoantibodies specific to that tumour marker protein detected using the immunoassay; where autoantibodies are quantified, the greater the level of cancer-associated auto-antibodies, the stronger the immune response. The tumour marker protein or proteins identified as eliciting the strongest immune response or responses in the patient (i.e. the highest level of autoantibodies) is or are then selected to form the basis of an anti-cancer vaccine for use in the patient.

In a further embodiment, the invention provides a method of monitoring whether vaccination of a subject with an anti-cancer vaccine based on a particular tumour marker protein has been successful in eliciting a humoral immune response (i.e. antibodies against the said tumour marker protein). This method is based on the same immunoassay methodology used to measure cancer-associated anti-tumour autoantibodies (i.e. use of an immunoassay reagent based on tumour marker protein purified from a body cavity fluid or an excretion taken from a cancer patient), the only difference being what is measured in the assay is an antibody response rather than an autoantibody response.

In this embodiment a sample of bodily fluid taken from a patient previously treated with the anti-cancer vaccine (e.g. an immunogenic preparation comprising the relevant tumour marker protein, or an antigenic fragment thereof or a vaccine comprising a nucleic acid encoding said relevant tumour marker protein) is contacted with an immunoassay reagent and complexes formed by specific binding of the immunoassay reagent to cancer-associated antibodies present in the sample are detected. The immunoassay reagent again comprises a sample of the said tumour marker protein prepared from bodily fluid derived from a body cavity or space as defined herein from one or more cancer patients and/or tumour marker protein prepared from an excretion from one or more cancer patients.

In addition to clinical applications in the detection of cancer, etc., the method of the invention may be used in any application where it is desired to test for the presence of cancer-associated anti-tumour autoantibodies. For example, the method of the invention may have applications in the laboratory as a research tool.

The tumour marker protein preparations provided by the invention are advantageously used as (components of) immunoassay reagents for use in the assay methods of the invention. However, the utility of the tumour marker protein preparations is not limited to such use. For example, they too may have applications in the laboratory as research tools. Moreover, it is possible for tumour marker proteins to have utility as therapeutic agents. The availability of large quantities of protein as provided by the bodily fluids defined herein allows pre-clinical and clinical testing, either in vitro or in vivo in humans or non-human animals, to determine efficacy of particular tumour marker proteins as therapeutic agents. Such testing methods would be applicable to each or all of the various tumour marker proteins described herein.

Another utility for tumour marker preparations of the invention is as a calibration material to be used in conjunction with the development of diagnostic tests for the presence of cancer or risk of cancer, which tests are based upon determination of the presence and/or level of any particular tumour marker protein in a clinical sample from a patient. The tumour marker protein preparations of the invention can be used to construct calibration curves for such tests. In particular this aspect of the invention includes:

A method of calibrating an assay for measurement or detection of a given tumour marker protein in a clinical sample which method comprises the steps of:

a) preparing at least two samples of a tumour marker protein prepared according to the method of the invention, each of which comprises said given tumour marker protein and each of which has a different tumour marker protein concentration to each of the other said samples:

b) carrying out a quantitative measurement of the concentration of said tumour marker protein in each of said samples using:

i) a spectrometric or spectrophotometric method and/or,
ii) an antibody reagent to said tumour marker protein, and c) constructing a standard curve for tumour marker protein concentration based on the measurements obtained in step (b).

Such standard curves may be constructed for any or all of the specific tumour marker proteins described herein.

The invention will be further understood with reference to the following experimental Examples, together with the accompanying Figures in which.

EXAMPLE 1

Figure 1:
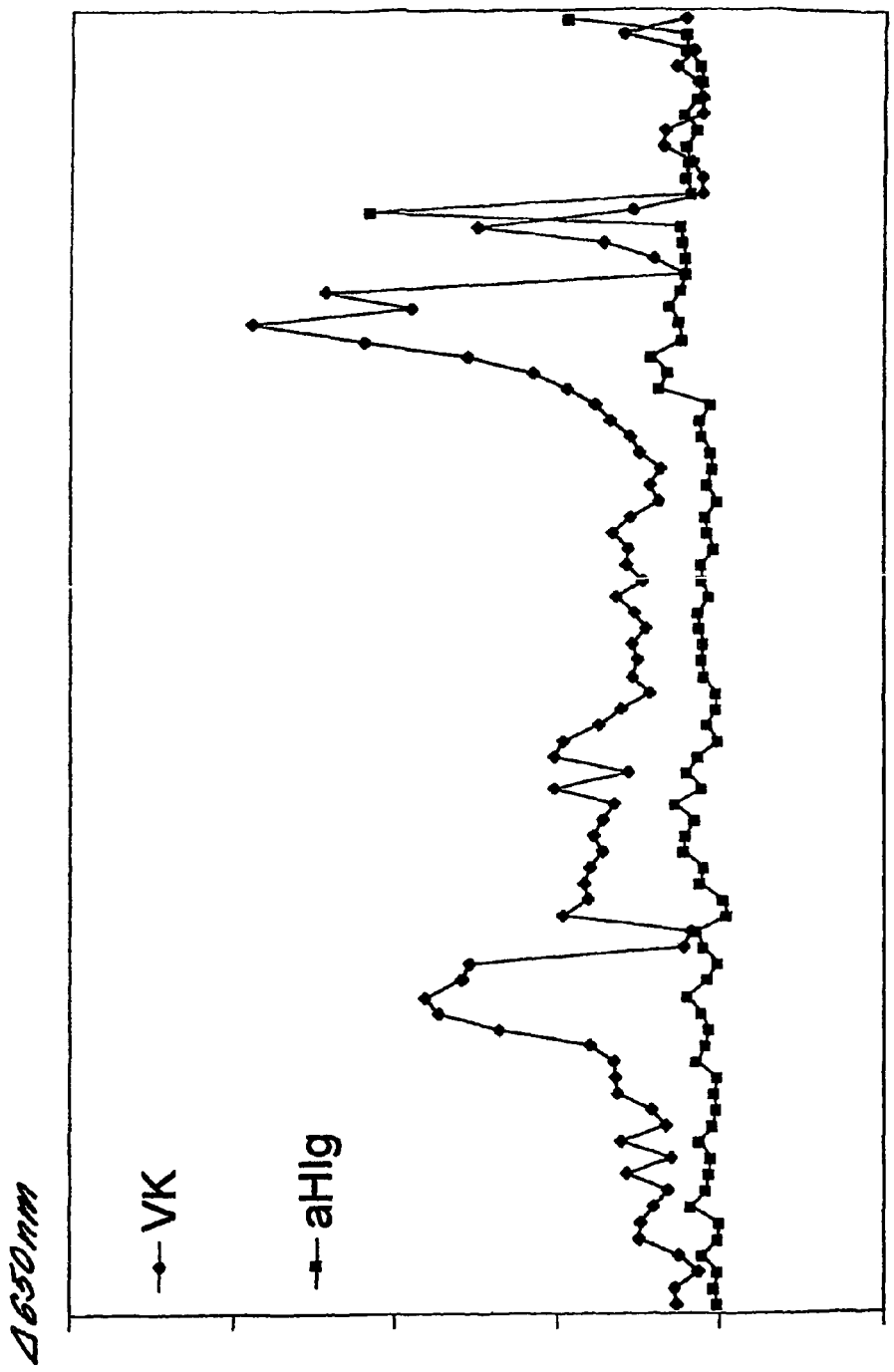
FIG. 1 shows a post-Ig disruption gel filtration chromatogram of a preparation of MUC16 (CA125) from ascites.

General Protocol for Purification of MUC1 Antigen

Monoclonal anti-MUC1 antibody B55 (also known as NCRC 11, Xoma Corporation) is conjugated to CNBr-sepharose beads. Other anti-MUC1 monoclonal antibodies may be substituted for B55.

Tumour-induced body fluids (e.g. pleural effusion, ascites, seroma or wound drainage fluid) are diluted 1/10 with phosphate buffered saline (PBS) and filtered to 0.45 μm.

Diluted body fluids are incubated with the anti-MUC1 sepharose beads (25 ml diluted fluid to 1 ml packed volume of beads) overnight at 4° C. with rolling ("batch" method) or re-circulated overnight through a packed column containing anti-MUC1 sepharose beads ("column" method).

"Batch" Method:

Beads are packed by centrifugation and the supernatant removed;

Beads re-suspended in 5-10 ml PBS and rolled for 10 mins then packed by centrifugation and the supernatant removed; repeat 5 times (or until $A_{280\ nm}$~0)

Beads re-suspended in 5 ml 100 mM DEA pH 11, and rolled at room temperature for 10 mins;

Beads packed by centrifugation and the supernatant removed, pH adjusted to 7 by the addition of pH 7 Tris buffer, dialysed against PBS for 24 hours minimum (100 DEA fraction);

Beads re-suspended in 5 ml PBS and rolled for 10 mins then packed by centrifugation and the supernatant removed, pH adjusted to 7 by the addition of pH 7 Tris buffer, dialysed against PBS for 24 hours minimum (post-DEA fraction);

MUC1 content of each fraction confirmed by ELISA using, for instance, the monoclonal anti-MUC1 antibody C595 (available from Cancer Research Campaign Laboratories, UK) (see example 5 for details) or B55; prior to pooling of the two fractions and storage at −20° C.

"Column" Method:—

Column washed with 5 column volumes of PBS, or until eluate reads ~0 at $A_{280\ nm}$;

1 column volume of 100 mM DEA pH11 applied, followed by 5 column volumes of PBS;

Eluate fractions (2 ml) collected from the time of DEA application through the application of PBS;

Fractions dialysed overnight against PBS;

Fractions assayed for MUC1 content by ELISA using, for instance, the monoclonal anti-MUC1 antibody C595 or B55, prior to pooling MUC1 positive fractions and storage at −20° C.

In order to remove contaminating immunoglobulins, MUC1 pooled fractions are incubated with dithiothreitol (DTT) to 50 mM for 30 mins, then iodoacetamide (to 75 mM) before being subjected to gel filtration on an S300 column.

Resulting fractions (5 ml) are assayed for MUC1 and human immunoglobulin (Ig) content by ELISA.

MUC1 containing fractions (uncontaminated with human Ig) are pooled and stored at −20° C.

EXAMPLE 2a

General Protocol for Purification of MUC16 Antigen (Previously Known as CA125)

One volume (e.g. 50 ml) of saturated ammonium sulphate was added to one volume (e.g. 50 ml) of tumour-induced body fluid (e.g. pleural effusion, ascites, seroma or wound drainage fluid) and incubated overnight at 4° C.

The resultant precipitate is collected by centrifugation (3500 rpm for 30 min in a standard benchtop centrifuge) and resuspended in ½ volume PBS.

This resuspension is subjected to gel filtration chromatography through an S300 column (2.5×100 cm) using PBS as the eluting buffer.

Fractions (5 or 10 ml) are collected and assayed by ELISA for MUC16, using for instance anti-CA125 from ICN or the anti-MUC16 antibody VK8 (Memorial Sloane Kettering, New York), prior to pooling MUC16 positive fractions and storage at −20° C.

In order to remove contaminating immunoglobulins, MUC16 pools are incubated with NaSCN (to 1.5M) for 10 mins, DTT (to 50 mM) for 30 mins, then iodoacetamide (to 75 mM) for 30 mins before being subjected to gel filtration on, for instance, an S300 or a Superdex™ 75 column.

Resulting fractions (5 ml) are assayed for MUC16 and human immunoglobulin (Ig) content by ELISA.

MUC16 containing fractions (uncontaminated with human Ig) are pooled and stored at −20° C.

EXAMPLE 2b

Post Ig Disruption Gel Filtration Chromatography

For a sample prepared in the manner described above, fractions from a post-Ig disruption gel filtration were assayed for MUC16 using anti-MUC16 antibody VK8 and for human Ig using an anti-human Ig. The results are shown in FIG. 1. As is clearly demonstrated, two substantially immunoglobulin free MUC16 peaks are eluted.

EXAMPLE 3

Purification of c-myc Antigen

Methodology as per purification of MUC1 (Example 1), except that:

Monoclonal anti-c-myc antibody 9E10 (ATCC) is used (or equivalent anti-c-myc antibody).

Gel filtration is performed on SUPERDEX™ 75 gel filtration column.

Electrophoresis and Western Blotting

Purity of MUC1, MUC16 and c-myc fractions are assessed by denaturing polyacrylamide gel electrophoresis and Western blotting, performed according to standard protocols using BIO-RAD™ MINI PROTEAN III™ gel electrophoresis assembly system and BIO-RAD™ DRYBLOT™ protein transfer assembly system.

Figure 2:
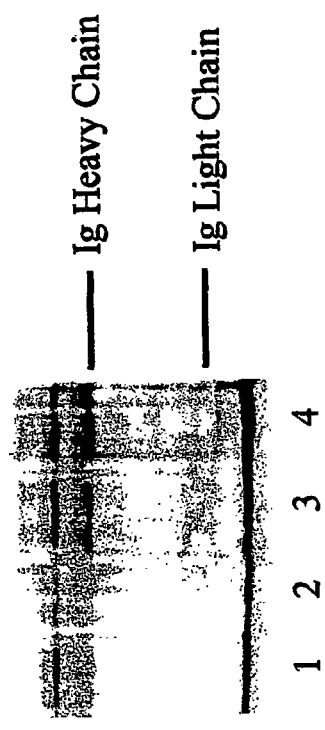
FIG. 2 shows a silver stained gel of c-myc purification from ascitic fluid, post immunoaffinity chromatography.
Figure 3:
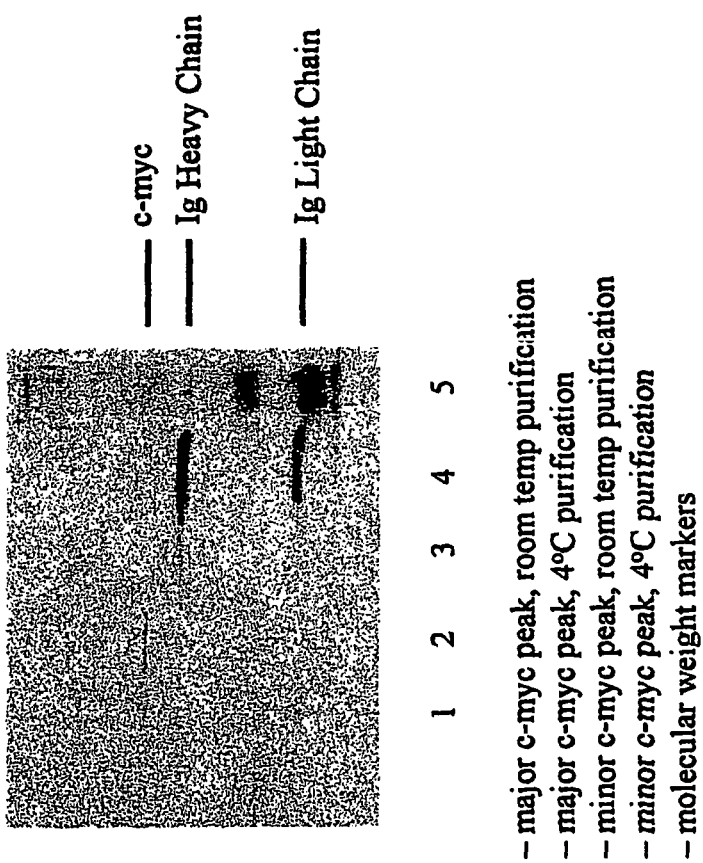
FIG. 3 shows an immunoprobed blot, c-myc purification from ascitic fluid, post immunoaffinity chromatography.

Protein patterns were revealed on gels for c-myc by silver staining (FIG. 2). Western blots of c-myc were immuno-probed using monoclonal antibodies 9E10 (FIG. 3). In each case, c-myc as well as immunoglobulin heavy and light chains are identified.

EXAMPLE 4

Standard Auto-Antibody Assay

Tumour antigen (e.g. MUC1, MUC16 or c-myc prepared according to Examples 1-3) diluted appropriately in PBS is plated out at 50 µl per well in a standard 96 well microtiter plate and left to air dry overnight;

Plate washed once with PBS/TWEEN™ washing buffer to remove residual salt crystals.

Plate blocked for 60 mins with 0.1% casein or 1% BSA in PBS;

Plate washed ×3 with PBS/TWEEN™ washing buffer;

Serum (diluted 1/100 in PBS/0.1% casein) plated out in triplicate (50 µl per well), also monoclonal antibody controls;

Incubate for 60 mins at room temperature with shaking;

Plate washed ×4 with PBS/TWEEN™ washing buffer;

Add horseradish peroxidase (HRP)-conjugated anti-Ig antibody (Dako) to each well (50 µl per well) at 1/8000 dilution for anti-human and 1/1000 for anti-mouse;

Incubate for 60 minutes at room temperature with shaking;

Wash plate ×4 with PBS/TWEEN™ washing buffer.

Add 50 µl TMB (tetramethylbenzadine) per well and read kinetically over a 10 min period at $A_{650\ nm}$.

Experimental Data

Figure 5:
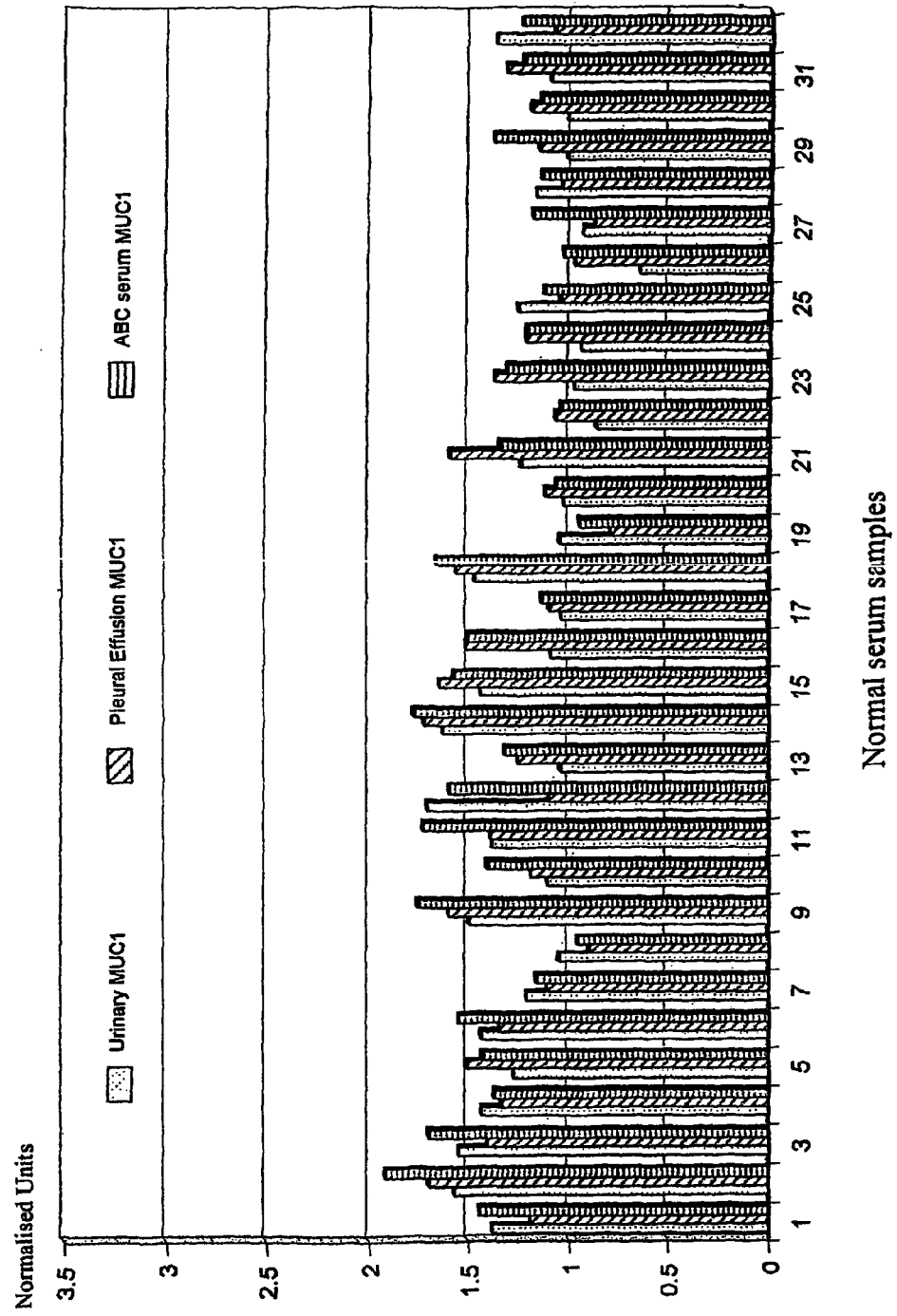
FIG. 5 shows autoantibody reactivity in serum from normal individuals against MUC1 from various body fluids: urinary MUC1 (normal), pleural effusion from a cancer patient and from advanced breast cancer patients (ABC serum)
Figure 6:
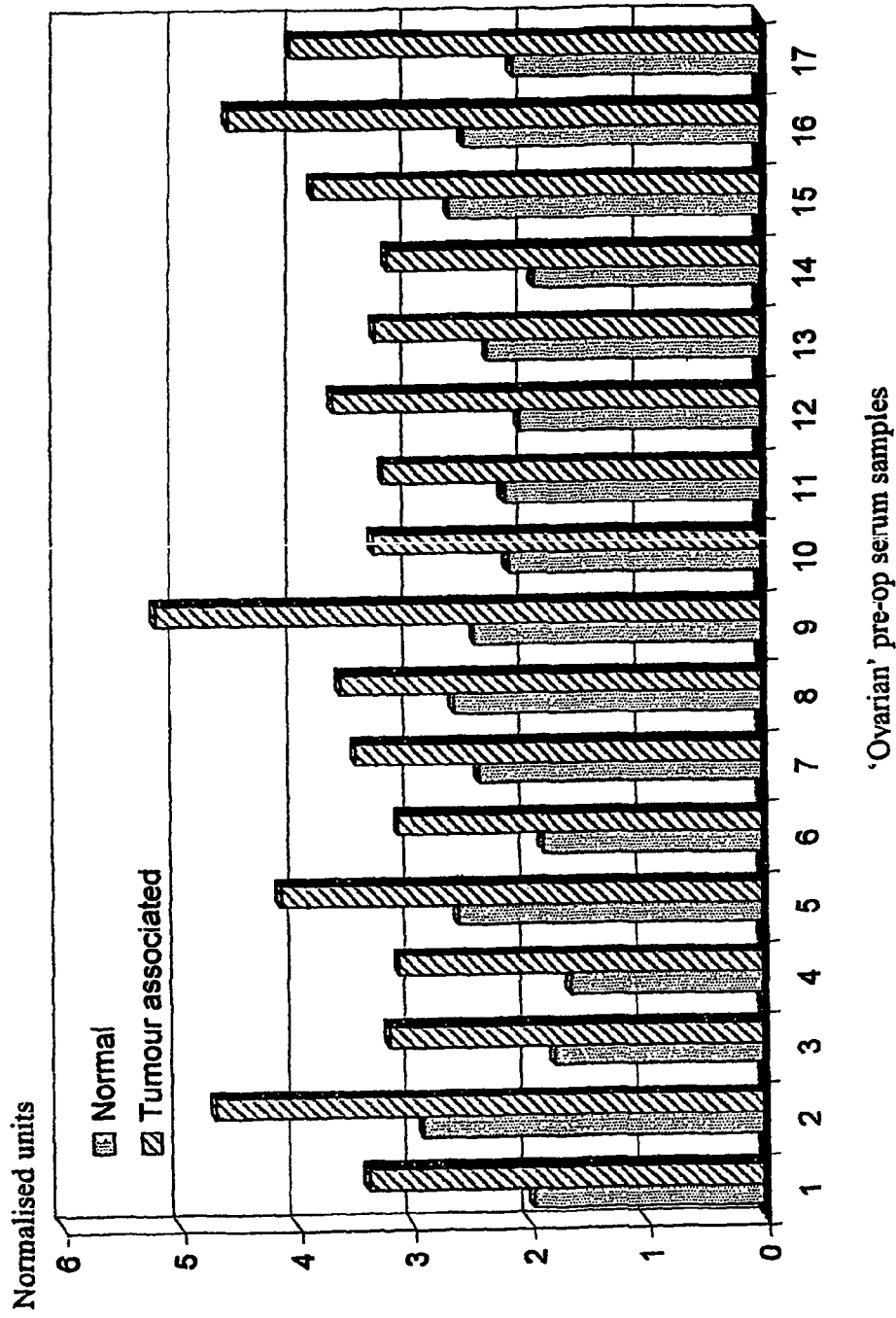
FIG. 6 shows the autoantibody reactivity in serum samples from pre-operative patients with ovarian masses against normal MUC16 (CA125) and against tumour-associated MUC16 from ascites.

Using the method as described in Example 4, cancer-associated autoantibodies to MUC1 and MUC16 were measured in a variety of sera using MUC1 and MUC16 isolated from the various sources as described herein. Results generated are shown in FIGS. 4 to 6.

Figure 4:
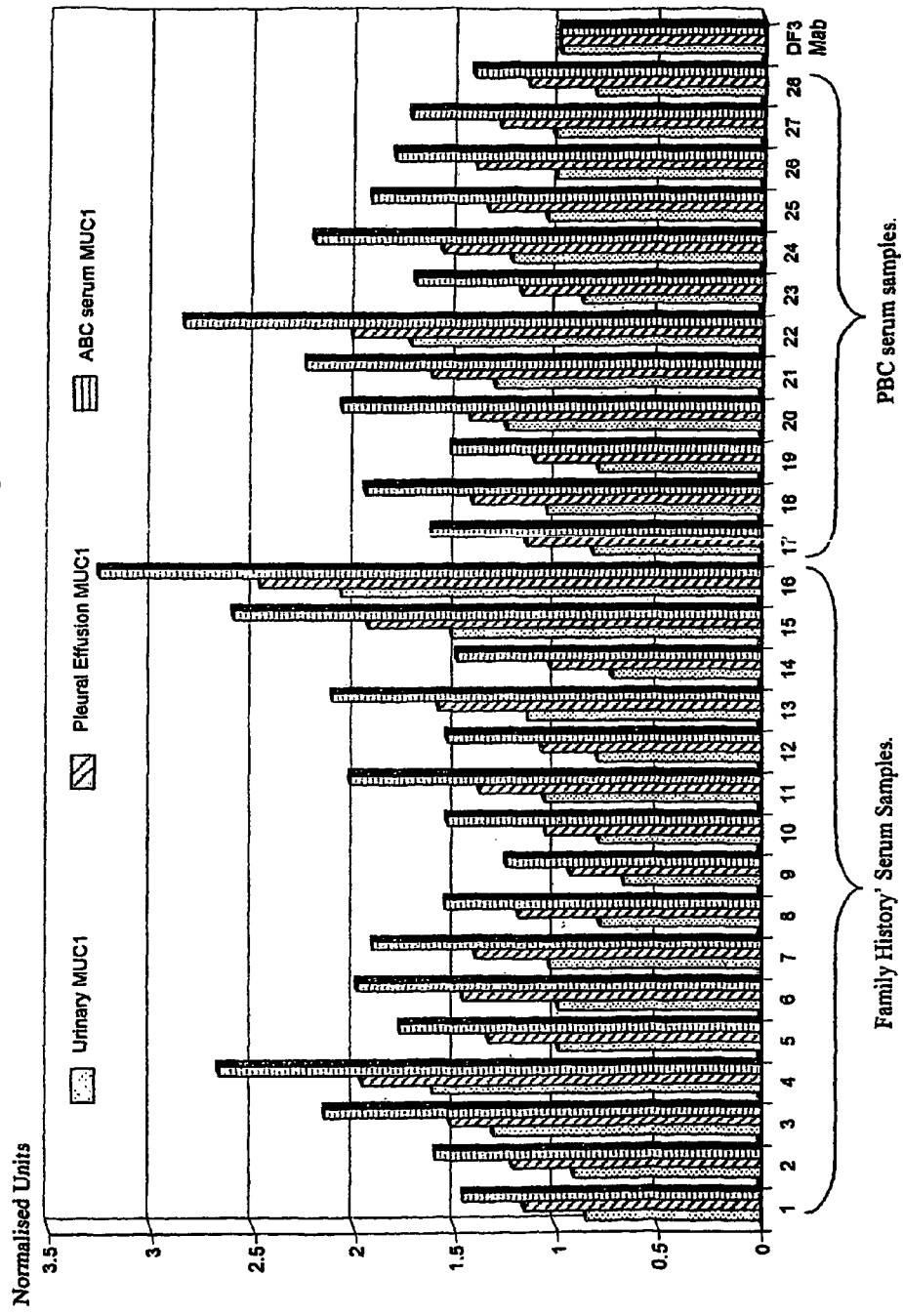
FIG. 4 shows a comparison of patient serum (patients with no evidence of breast cancer themselves but with a family history of breast cancer and those with primary breast cancer) auto-antibody reactivity against MUC1 isolated from various body fluids: urine (from "normal" individuals), pleural effusion from a cancer patient and serum from advanced breast cancer patients (ABC serum)

FIG. 4 shows a comparison of patient serum auto-antibody reactivity against MUC1 isolated from various body fluids: urine (from "normal" individuals), pleural effusion from a cancer patient and serum from advanced breast cancer patients (ABC serum). The patient serum tested was from either individuals with no evidence of breast cancer themselves but with a family history of breast cancer (i.e. one or more relatives who had breast cancer at a young age) or individuals with primary breast cancer.

Standard auto-antibody ELISAs were performed as described above, utilising MUC1 isolated from urine (normal), pleural effusion or ABC serum as antigen. Data was normalised to an internal control reaction using the DF3 anti-MUC1 monoclonal antibody (as opposed to a serum sample) against each of the MUC1 antigens.

As can be seen from the Figure, MUC1 derived from normal urine (nMUC1) was consistently lower in its reactivity than MUC1 derived from either pleural effusion (PE) or ABC serum. Furthermore, MUC1 derived from PE was of similar reactivity to cancer-associated MUC1 autoantibodies as MUC1 isolated from the serum of patients with ABC and therefore of equal diagnostic value.

FIG. 5 shows the results of an identical exercise to FIG. 4 except that all serum samples tested were for normal individuals (no breast cancer or family history of breast cancer). As can be seen, there is no significant difference in the reactivity of the serum to the three different antigens.

FIG. 6 shows reactivity of MUC16 cancer-associated autoantibodies from serum of patients with ovarian masses (pre-operative) against MUC16 (CA125) isolated from the serum of normal individuals and from ascites fluid in a patient with breast cancer. Antigens were prepared as in Example 2 and autoantibodies detected using ELISA assay as described in Example 4.

As can be seen, greatly enhanced reactivity of the cancer-associated MUC16 autoantibodies is seen with the MUC16 antigen from ascites fluid as compared to the "normal" MUC16. This experimental result therefore confirms the usefulness of ascites fluid as an antigen source for detection of cancer-associated autoantibodies.

EXAMPLE 5

Measurement of Cancer-Associated MUC1 Levels in Ascites Fluid, Pleural Effusion, Seroma and Wound Drainage Fluid MUC1 levels found in the serum of a patient with cancer were compared with the levels found in ascites fluid, pleural effusion, wound drainage fluid or seroma, in each case in the same patient from whom the serum sample was taken. MUC1 in the samples was quantified according to the following protocol:

Capture MUC1 ELISA Protocol

Aliquot 50 µl per well antibody solution into triplicate wells of a microtitre plate (usually 1 µg $ml^{-2}$ C595 (IgG) and appropriate negative control) and incubate at RT with shaking for 1 hr for the protein to adsorb to the plate.

Wash the plate ×4 with PBS/TWEEN™ washing buffer using 250 µl per well.

Block the plate using 1% BSA 100 µl per well and incubate at RT with shaking for 1 hr.

Wash the plate ×4 with PBS/TWEEN™ washing buffer using 250 µl per well.

Apply 50 µl per well of fluid being tested, diluted 1/10 in PBS and incubate at RT with shaking for 1 hr.

Wash the plate ×4 with PBS/TWEEN™ washing buffer using 250 µl per well.

Add 50 µl per well biotinylated C595 (1 µg/ml) and incubate at RT with shaking for 1 hr.

Wash the plate ×4 with PBS/TWEEN™ washing buffer using 250 µl per well.

Add 50 µl per well extra-avidin peroxidise at 1/1000 dilution and incubate at RT with shaking for 1 hr.

Wash the plate ×4 with PBS/TWEEN™ washing buffer using 250 µl per well.

Add 50 µl per well TMB substrate and read kinetically at $650_{nm}$ for 10 minutes.

Figure 7:
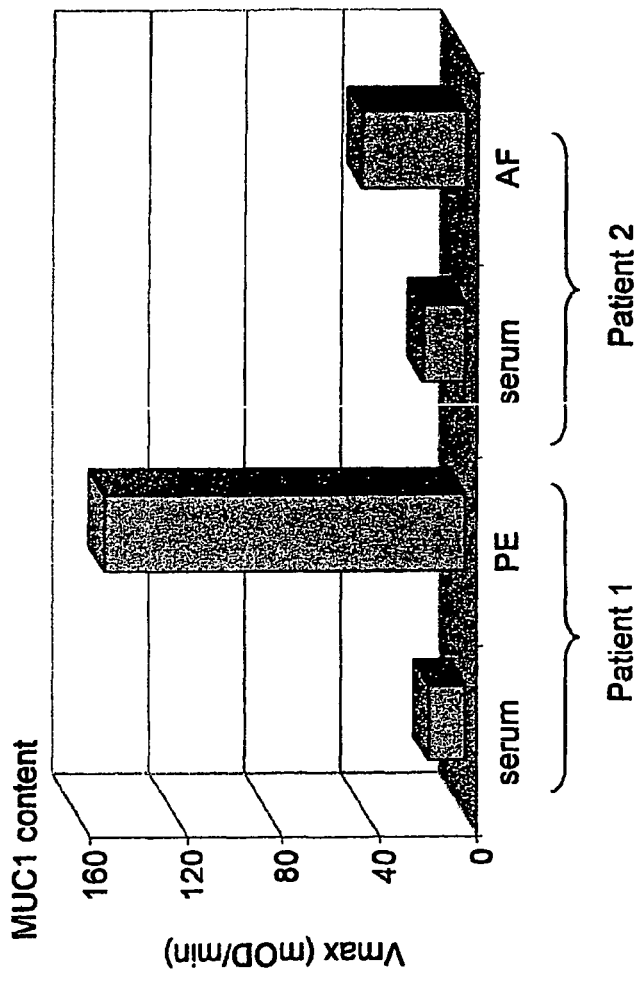
FIG. 7 shows the cancer-associated MUC1 concentration in sera, pleural effusion and ascitic fluid.
Figure 8:
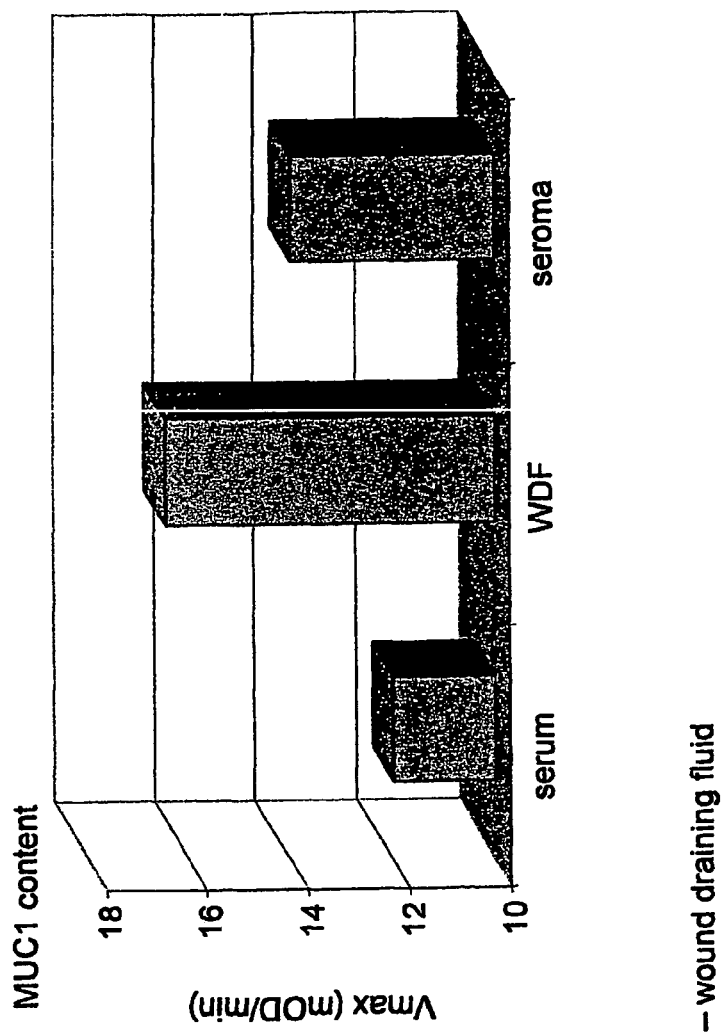
FIG. 8 shows the cancer-associated MUC1 concentration in serum, wound drainage fluid and in seroma.

The results are shown in FIGS. 7 and 8.

As will be readily apparent from the data serum levels of the cancer-associated MUC1 antigen are significantly lower than the level found in either ascites fluid, pleural effusion, seroma or wound drainage fluid. Accordingly, there are substantial benefits to be gained in terms of yield in recovering tumour marker antigen from those body cavity fluids.

EXAMPLE 6

Reactivity of Human Anti-MUC1 Antibodies Purified Against Cancer-Associated MUC1 from Seroma Human antibodies from seroma from patient M were purified by immunoaffinity chromatography against MUC1 derived from seroma fluid from the same cancer patient M. Purified antibodies were then tested against BSA conjugated protein core peptide to MUC1 and MUC1 derived from:— patient M's urine taken two years prior to cancer diagnosis; patient M's seroma taken after cancer diagnosis. The antibody purification from seroma was carried out according to the following protocol:

Human Anti-MUC1 Antibody Purification

Purification of human anti-MUC1 auto-antibodies was by affinity chromatography.

Seroma fluid, diluted 10 fold in PBS pH 7.6, was applied at 0.5 ml/min by overnight re-circulation at 4° C., to an affinity matrix in column format, consisting of CNBr sepharose (Pharmacia) coupled (following the manufacturers instructions) to Pt-MUC1.

After seroma fluid application, the column was washed with 15 ml of PBS (ensuring return of $A_{280}$nm reading to zero) prior to elution of antibody using 10 ml of 3M NaSCN, at 1 m/min.

Fractions of 1 ml were collected throughout, desalted by dialysis against PBS and tested by ELISA for the presence of antibody.

Positive fractions were pooled, purity of antibody verified (by PAGE) and antibody concentration determined.

Assay of the purified antibodies against the three MUC1 antigens identified above was carried out according to the following protocol:

MUC1 ELISA Protocol

Aliquot 50 µl per well of the MUC1 antigen solution into triplicate wells of a microtitre plate and dry down at RT overnight.

Wash the plate ×2 with PBS/TWEEN™ washing buffer using 250 µl per well.

Block the plate with 1% BSA using 100 µl per well and incubate at RT with shaking for 1 hr.

Wash the plate ×2 with PBS/TWEEN™ washing buffer using 250 µl per well.

Add 50 µl per well purified antibody solution at 1 µg/ml and incubate at RT with shaking for 1 hr.

Wash the plate ×4 with PBS/TWEEN™ washing buffer using 250 µl per well.

Add 50 µl per well α-human Ig HRP (DAKO), freshly diluted as per manufacturers instructions, and incubate at RT with shaking for 1 hr.

Wash the plate ×4 with PBS/TWEEN™ washing buffer using 250 µl per well.

Add 50 µl per well TMB substrate and read kinetically at $650_{nm}$ for 10 minutes.

Figure 9:
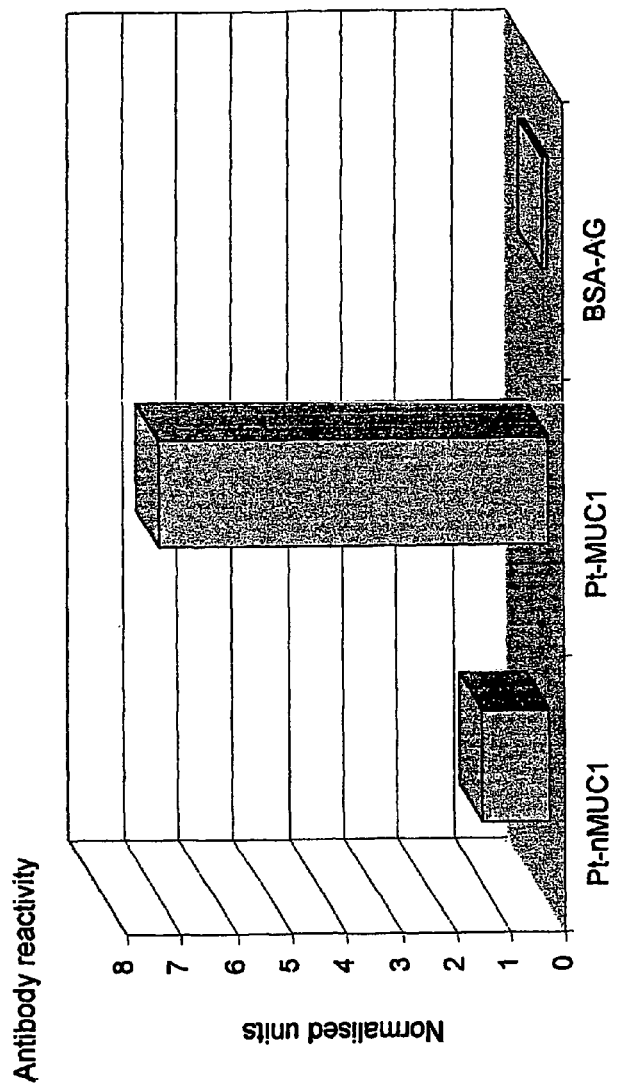
FIG. 9 shows the reactivity of purified autoantibodies from seroma of patient M with cancer against purified urinary MUC1 from patient M taken two years prior to cancer diagnosis, MUC1 derived from the seroma of patient M, after diagnosis with cancer and bovine serum albumen conjugated to MUC1 protein core peptide.

The results are shown in FIG. 9.

Reactivity of the antibodies against MUC1 peptide was negligible. Reactivity of antibodies against normal MUC1 was considerably lower than that seen towards patient M's seroma derived MUC1. It can be inferred from this result that normal MUC1 molecule is substantially different with regard to its immune recognition, to that found in seroma fluid from an individual with cancer.

EXAMPLE 7

Figure 10:
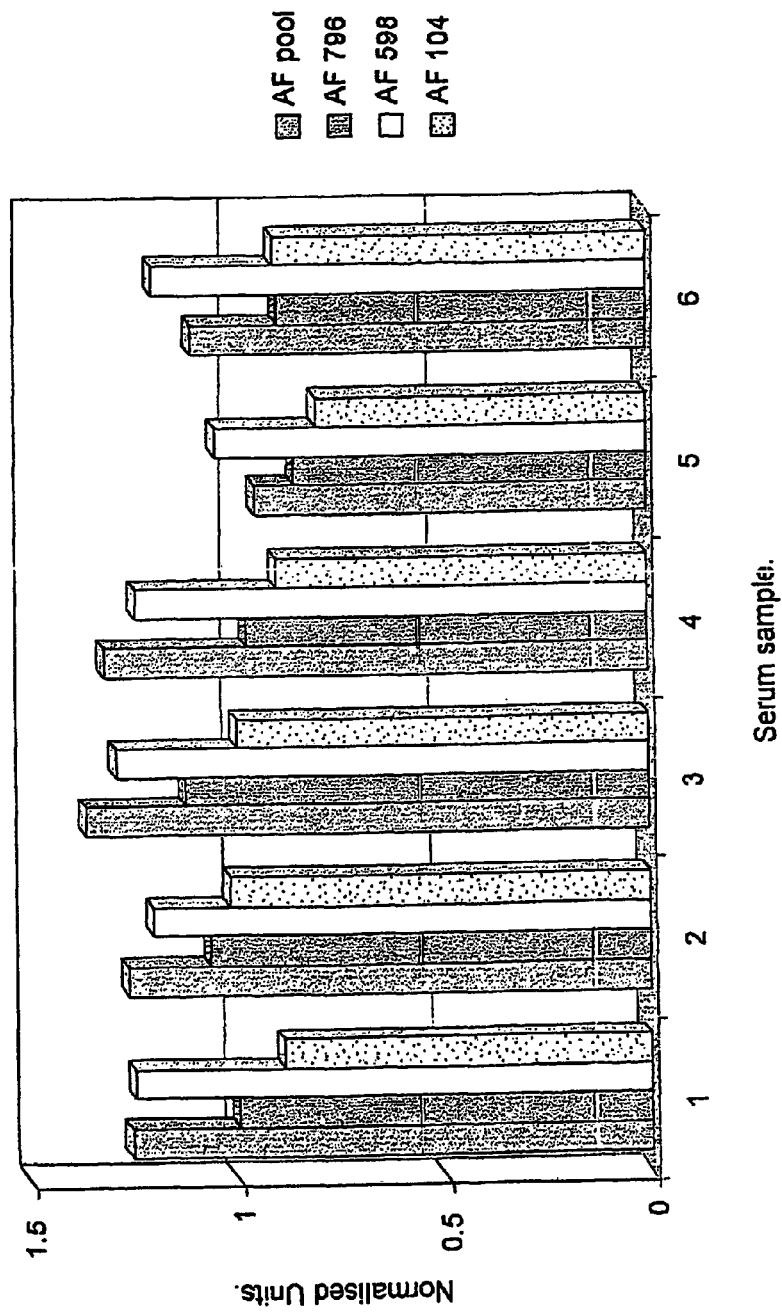
FIG. 10 shows serum autoantibody reactivity against MUC1 purified from pooled ascites fluid and against MUC1 purified from individual ascites samples from cancer patients.
Figure 11:
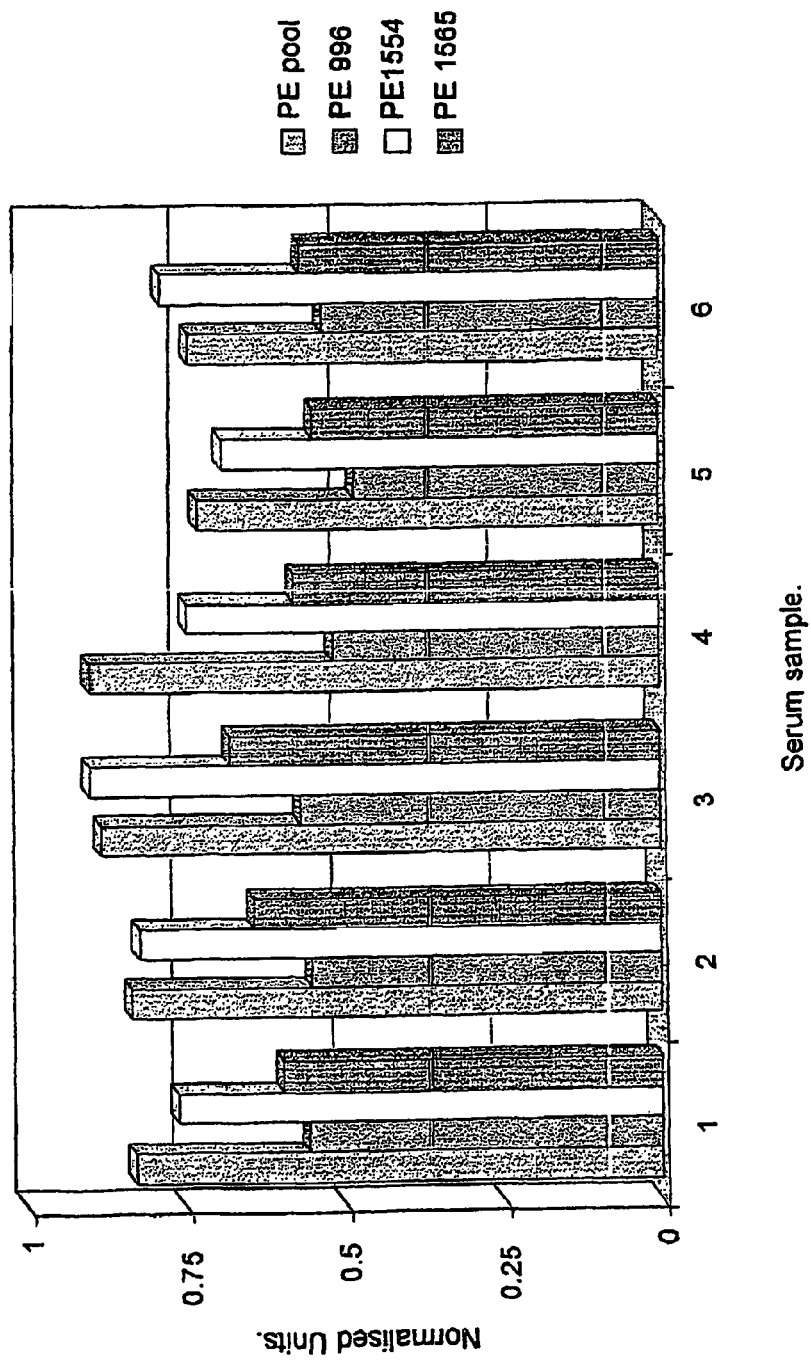
FIG. 11 shows serum autoantibody reactivity against MUC1 purified from pooled pleural effusions and against MUC1 purified from individuals pleural effusion samples from cancer patients.

Serum Reactivity Against MUC1 Purified from Pooled Ascitic Fluid and Pleural Effusions MUC1 was purified from pooled ascitic fluid and from pooled pleural effusion from patients with advanced breast cancer using the protocol described in Example 1 and its reactivity against serum from patients with primary breast cancer measured as described in Example 4. The antigen from the pooled fluids was compared in each case with antigen isolated from 3 individual samples of ascitic fluid or pleural effusion respectively from patients with ABC. The results are shown in FIGS. 10 and 11.

In the case of both ascitic fluid and pleural effusion the reactivity of the MUC1 from pooled fluid is as good as that isolated from individual samples. Furthermore, while there is great scope for variability of reactivity using samples from individuals, pooled samples provide greater consistency of product so that one would not expect the reactivity to significantly vary between batches from pooled samples.

EXAMPLE 8

Calibration Curve using MUC1

Serial dilutions of MUC1 which had been isolated from pleural effusion were prepared. Their MUC1 concentrations were measured by the method as shown in example 4 except that no human sera were used. Detection was by mouse B55 antibody followed by Dako anti-mouse HRP using an endpoint rather than a kinetic reading.

Figure 12:
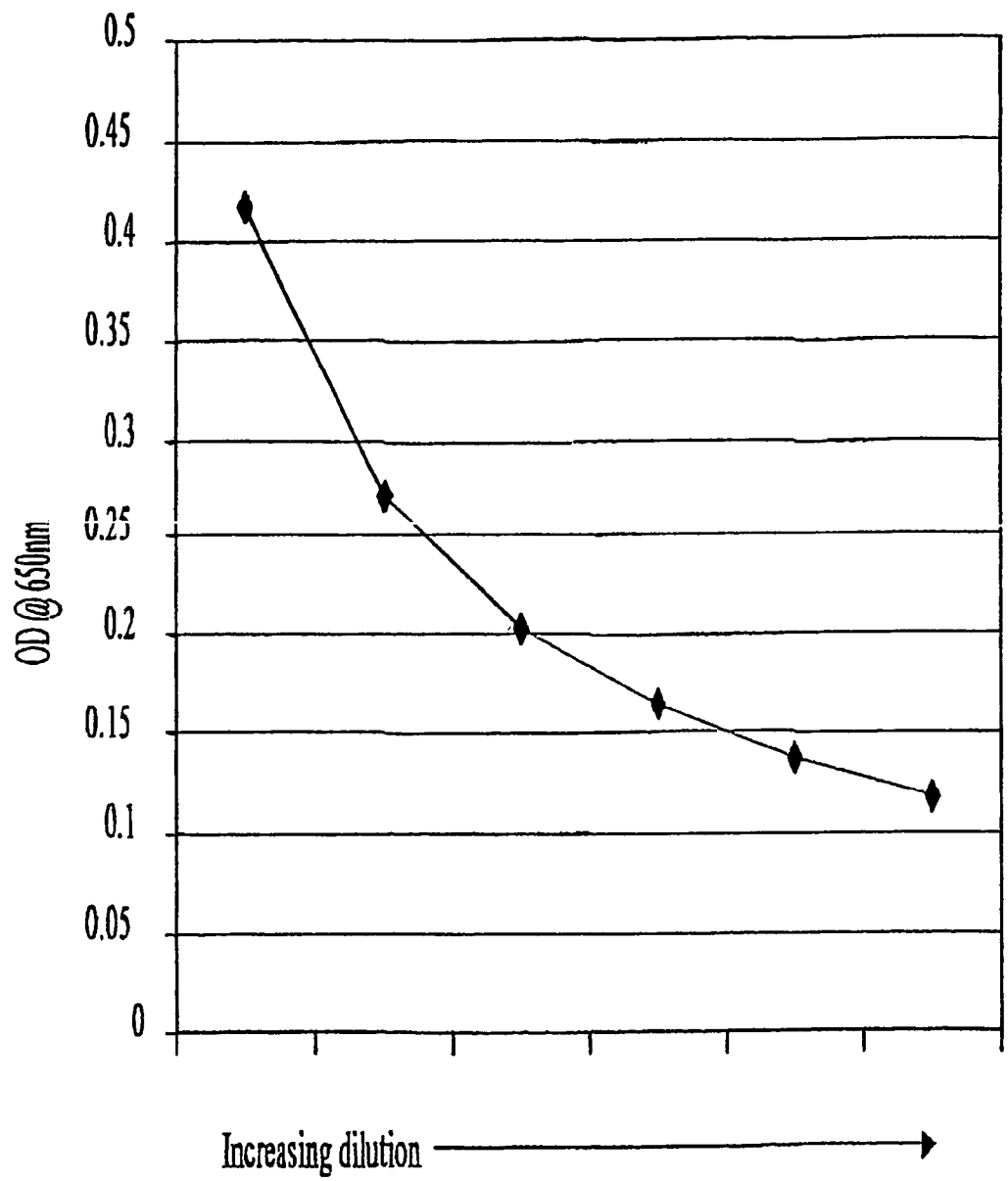
FIG. 12 shows a calibration curve prepared from MUC1 from a pleural effusion.

The results are shown in FIG. 12 and confirm the utility of the tumour marker proteins prepared in accordance with the invention as a calibration material.

Sources of Antibodies to Tumour Marker Proteins

The following lists sources of antibodies which may be used in the purification of tumour marker proteins by affinity chromatography. Affinity chromatography may be performed following the general methodology described in Example 1 (in relation to MUC1), with appropriate modification. It will be appreciated that other antibodies specific for the relevant marker protein may also be used.

Carcinoembryonic Antigen (CEA):

1116NS-3d, ATCC number CRL-8019, B lymphocyte hybridoma producing monoclonal antibody against CEA; T84.66A3.1A.1F2, ATCC number HB-8747, B lymphocyte hybridoma producing monoclonal antibody against CEA.

P53:

Rabbit anti-human p53 polyclonal, commercially available from from Serotec Ltd, Kidlington, oxford OX5 1JE, United Kingdom.

Monoclonal anti-p53, clone BP53-12, commercially available from Sigma.

CA19-9:

Mouse anti-human CA19-9 monoclonal, type clone 1116-NS-19-9, IgGl, commercially available from from Serotec Ltd, Kidlington, Oxford OX5 1JE, United Kingdom.

H-ras p21:

Rabbit polyclonal IgG, commercially available from Santa Cruz Biotechnology, Inc., Santa Cruz, Calif., USA.

BRCA1:

Rabbit polyclonal IgG, commercially available from Santa Cruz Biotechnology, Inc., Santa Cruz, Calif., USA.

BRCA2:

Goat polyclonal IgG, commercially available from Santa Cruz Biotechnology, Inc., Santa Cruz, Calif., USA.

APC:

Rabbit polyclonal IgG, commercially available from Santa Cruz Biotechnology, Inc., Santa Cruz, Calif., USA.

PSA:

Mouse monoclonal IgG, commercially available from Santa Cruz Biotechnology, Inc., Santa Cruz, Calif., USA.

The invention claimed is:

1. A method of detecting or diagnosing cancer in a patient in need of detection or diagnosis of cancer, comprising:
    contacting a bodily fluid sample from the patient in need of detection or diagnosis of cancer with an immunoassay reagent and detecting a presence of complexes formed by specific binding of the immunoassay reagent to any cancer-associated anti-tumor autoantibodies present in the sample,
    wherein the immunoassay reagent comprises a panel of two or more tumor marker proteins, one or more of which having been prepared from a tumor-induced bodily fluid produced in a body cavity or space in the presence of the tumor of one or more cancer patients, wherein the bodily fluid contains more cancer-associated forms of the tumor marker protein than a non-tumor-induced bodily fluid in the same patient, and the bodily fluid is not a fluid derived from the systemic circulation,
    wherein at least one of the two or more tumor marker proteins is MUC1, MUC16, c-myc, c-erbB2, p53, ras, BRCA1, BRCA2, APC, PSA, CEA or CA19.9, or a fragment thereof,
    wherein the two or more tumor marker proteins are two or more different tumor marker proteins or are two or more different epitopes on the same tumor marker protein,
    wherein the one or more tumor marker proteins prepared from a bodily fluid exhibit selective reactivity with cancer-associated anti-tumor autoantibodies, wherein the tumor marker proteins are over-expressed or altered forms of wild-type proteins,
    wherein detection of complexes indicates the presence of cancer-associated anti-tumor autoantibodies in the individual, and
    wherein detection of the presence of an elevated level of the anti-tumor autoantibodies in the sample, as compared to a sample from a normal control, indicates that the patient in need of detection or diagnosis of cancer has or is developing a cancer.

2. The method of claim 1, wherein the bodily fluid is ascites fluid, pleural effusion, seroma, hydrocoele or wound drainage fluid.

3. The method of claim 1, wherein the one or more tumor marker proteins that is MUC1, MUC16, c-myc, c-erbB2, p53, ras, BRCA1, BRCA2, APC, PSA, CEA or CA19.9, or a fragment thereof, is
    the one or more tumor marker proteins prepared from the bodily fluid.

4. The method of claim 1 wherein the one or more tumor marker proteins prepared from the bodily fluid are prepared by collecting bodily fluid from the body cavity or space in which a tumor is or was present from one or more cancer patients and isolating the tumor marker protein from the bodily fluid using protein purification techniques.

5. The method of claim 1 wherein the one or more tumor marker proteins prepared from the bodily fluid are prepared by collecting bodily fluid from the body cavity or space in which a tumor is or was present from two or more cancer patients, pooling the bodily fluid and isolating the tumor marker protein from the pooled bodily fluid using protein purification techniques.

6. The method of claim 4 wherein the isolated tumor marker protein is substantially immunoglobulin free.

7. The method of claim 1 where the bodily fluid from which the one or more tumor marker proteins is prepared is not whole blood or serum.

8. The method of claim 1 wherein the bodily fluid is produced during the disease process in response to or as a consequence of the presence of tumor cells.

9. The method of claim 1 wherein the cancer patient from which the tumor-induced bodily fluid is prepared is the same as the individual from which the sample was obtained.

10. A method of detecting or diagnosing cancer in a patient in need of monitoring of progress of cancer or other neoplastic disease, comprising:
    contacting a bodily fluid sample from the patient in need of monitoring of progress of cancer or other neoplastic disease with an immunoassay reagent and detecting a presence of complexes formed by specific binding of the immunoassay reagent to any cancer-associated anti-tumor autoantibodies present in the sample,
    wherein the immunoassay reagent comprises a panel of two or more tumor marker proteins, one or more of which having been prepared from a tumor-induced bodily fluid produced in a body cavity or space in the presence of the tumor of one or more cancer patients, wherein the bodily fluid contains more cancer-associated forms of the tumor marker protein than a non-tumor-induced bodily fluid in the same patient, and the bodily fluid is not a fluid derived from the systemic circulation,
    wherein at least one of the two or more tumor marker proteins is MUC1, MUC16, c-myc, c-erbB2, p53, ras, BRCA1, BRCA2, APC, PSA, CEA or CA19.9, or a fragment thereof, wherein the two or more tumor marker proteins are two or more different tumor marker proteins or are two or more different epitopes on the same tumor marker protein, wherein the one or more tumor marker proteins prepared from a bodily fluid exhibit selective reactivity with cancer-associated anti-tumor autoantibodies, wherein the tumor marker proteins are over-expressed or altered forms of wild-type proteins, wherein detection of complexes indicates the presence of cancer-associated anti-tumor autoantibodies in the individual, and wherein detection of the presence of an elevated level of the anti-tumor autoantibodies in the sample, as compared to a sample from a normal control, indicates the progress of cancer or other neoplastic disease in the patient in need of monitoring of progress of cancer or other neoplastic disease.

11. The method of claim 10 wherein the bodily fluid is ascites fluid, pleural effusion, seroma, hydrocoele or wound drainage fluid.

12. The method of claim 10 wherein the one or more tumor marker proteins that is MUC1, MUC16, c-myc, c-erbB2, p53, ras, BRCA1, BRCA2, APC, PSA, CEA or CA19.9, or a fragment thereof, is the one or more tumor marker proteins prepared from the bodily fluid.

13. The method of claim 10 wherein the one or more tumor marker proteins prepared from the bodily fluid are prepared by collecting bodily fluid from the body cavity or space in which a tumor is or was present from one or more cancer patients and isolating the tumor marker protein from the bodily fluid using protein purification techniques.

14. The method of claim 10 wherein the one or more tumor marker proteins prepared from the bodily fluid are prepared by collecting bodily fluid from the body cavity or space in which a tumor is or was present from two or more cancer patients, pooling the bodily fluid and isolating the tumor marker protein from the pooled bodily fluid using protein purification techniques.

15. The method of claim 13 wherein the isolated tumor marker protein is substantially immunoglobulin free.

16. The method of claim 10 where the bodily fluid from which the one or more tumor marker proteins is prepared is not whole blood or serum.

17. The method of claim 10 wherein the bodily fluid is produced during the disease process in response to or as a consequence of the presence of tumor cells.

18. The method of claim 10 wherein the cancer patient from which the tumor-induced bodily fluid is prepared is the same as the individual from which the sample was obtained.

19. A method of detecting early neoplastic or early carcinogenic change in an asymptomatic subject, comprising:

contacting a bodily fluid sample from the subject with an immunoassay reagent and detecting a presence of complexes formed by specific binding of the immunoassay reagent to any cancer-associated anti-tumor autoantibodies present in the sample, wherein the immunoassay reagent comprises a panel of two or more tumor marker proteins, one or more of which having been prepared from a tumor-induced bodily fluid produced in a body cavity or space in the presence of the tumor of one or more cancer patients, wherein the bodily fluid contains more cancer-associated forms of the tumor marker protein than a non-tumor-induced bodily fluid in the same patient, and the bodily fluid is not a fluid derived from the systemic circulation, wherein at least one of the two or more tumor marker proteins is MUC1, MUC16, c-myc, c-erbB2, p53, ras, BRCA1, BRCA2, APC, PSA, CEA or CA19.9, or a fragment thereof, wherein the two or more tumor marker proteins are two or more different tumor marker proteins or are two or more different epitopes on the same tumor marker protein, wherein the one or more tumor marker proteins prepared from a bodily fluid exhibit selective reactivity with cancer-associated anti-tumor autoantibodies, wherein the tumor marker proteins are over-expressed or altered forms of wild-type proteins, wherein detection of complexes indicates the presence of cancer-associated anti-tumor autoantibodies in the individual, and wherein detection of the presence of an elevated level of the anti-tumor autoantibodies in the sample, as compared to a sample from a normal control, indicates early neoplastic or early carcinogenic change in the asymptomatic subject.

20. The method of claim 19 wherein the bodily fluid is ascites fluid, pleural effusion, seroma, hydrocoele or wound drainage fluid.

21. The method of claim 19 wherein the one or more tumor marker proteins that is MUC1, MUC16, c-myc, c-erbB2, p53, ras, BRCA1, BRCA2, APC, PSA, CEA or CA19.9, or a fragment thereof, is the one or more tumor marker proteins prepared from the bodily fluid.

22. The method of claim 19 wherein the one or more tumor marker proteins prepared from the bodily fluid are prepared by collecting bodily fluid from the body cavity or space in which a tumor is or was present from one or more cancer patients and isolating the tumor marker protein from the bodily fluid using protein purification techniques.

23. The method of claim 19 wherein the one or more tumor marker proteins prepared from the bodily fluid are prepared by collecting bodily fluid from the body cavity or space in which a tumor is or was present from two or more cancer patients, pooling the bodily fluid and isolating the tumor marker protein from the pooled bodily fluid using protein purification techniques.

24. The method of claim 22 wherein the isolated tumor marker protein is substantially immunoglobulin free.

25. The method of claim 19 where the bodily fluid from which the one or more tumor marker proteins is prepared is not whole blood or serum.

26. The method of claim 19 wherein the bodily fluid is produced during the disease process in response to or as a consequence of the presence of tumor cells.

27. The method of claim 19 wherein the cancer patient from which the tumor-induced bodily fluid is prepared is the same as the individual from which the sample was obtained.

28. A method of identifying risk of developing cancer in an asymptomatic human subject selected from a population of asymptomatic human subjects in need of a screening for a risk of developing cancer, comprising:

contacting a bodily fluid sample from the subject with an immunoassay reagent and detecting a presence of complexes formed by specific binding of the immunoassay reagent to any cancer-associated anti-tumor autoantibodies present in the sample, wherein the immunoassay reagent comprises a panel of two or more tumor marker proteins, one or more of which having been prepared from a tumor-induced bodily fluid produced in a body cavity or space in the presence of the tumor of one or more cancer patients, wherein the bodily fluid contains more cancer-associated forms of the tumor marker protein than a non-tumor-induced bodily fluid in the same patient, and the bodily fluid is not a fluid derived from the systemic circulation,
wherein at least one of the two or more tumor marker proteins is MUC1, MUC16, c-myc, c-erbB2, p53, ras, BRCA1, BRCA2, APC, PSA, CEA or CA19.9, or a fragment thereof,
wherein the two or more tumor marker proteins are two or more different tumor marker proteins or are two or more different epitopes on the same tumor marker protein,
wherein the one or more tumor marker proteins prepared from a bodily fluid exhibit selective reactivity with cancer-associated anti-tumor autoantibodies, wherein the tumor marker proteins are over-expressed or altered forms of wild-type proteins,
wherein detection of complexes indicates the presence of cancer-associated anti-tumor autoantibodies in the individual,
wherein detection of the presence of an elevated level of the anti-tumor autoantibodies in the sample, as compared to a normal control, identifies the asymptomatic subject as being at risk of developing cancer.

29. The method of claim 28 wherein the bodily fluid is ascites fluid, pleural effusion, seroma, hydrocoele or wound drainage fluid.

30. The method of claim 28 wherein the one or more tumor marker proteins that is MUC1, MUC16, c-myc, c-erbB2, p53, ras, BRCA1, BRCA2, APC, PSA, CEA or CA19.9, or a fragment thereof, is the one or more tumor marker proteins prepared from the bodily fluid.

31. The method of claim 28 wherein the one or more tumor marker proteins prepared from the bodily fluid are prepared by collecting bodily fluid from the body cavity or space in which a tumor is or was present from one or more cancer patients and isolating the tumor marker protein from the bodily fluid using protein purification techniques.

32. The method of claim 28 wherein the one or more tumor marker proteins prepared from the bodily fluid are prepared by collecting bodily fluid from the body cavity or space in which a tumor is or was present from two or more cancer patients, pooling the bodily fluid and isolating the tumor marker protein from the pooled bodily fluid using protein purification techniques.

33. The method of claim 31 wherein the isolated tumor marker protein is substantially immunoglobulin free.

34. The method of claim 28 where the bodily fluid from which the one or more tumor marker proteins is prepared is not whole blood or serum.

35. The method of claim 28 wherein the bodily fluid is produced during the disease process in response to or as a consequence of the presence of tumor cells.

36. The method of claim 28 wherein the cancer patient from which the tumor-induced bodily fluid is prepared is the same as the individual from which the sample was obtained.

37. A method of monitoring a response of a cancer patient to an anti-cancer treatment, comprising:
contacting a bodily fluid sample from the patient with an immunoassay reagent and detecting a presence of complexes formed by specific binding of the immunoassay reagent to any cancer-associated anti-tumor autoantibodies present in the sample,
wherein the immunoassay reagent comprises a panel of two or more tumor marker proteins, one or more of which having been prepared from a tumor-induced bodily fluid produced in a body cavity or space in the presence of the tumor of one or more cancer patients,
wherein the bodily fluid contains more cancer-associated forms of the tumor marker protein than a non-tumor-induced bodily fluid in the same patient, and the bodily fluid is not a fluid derived from the systemic circulation,
wherein at least one of the two or more tumor marker proteins is MUC1, MUC16, c-myc, c-erbB2, p53, ras, BRCA1, BRCA2, APC, PSA, CEA or CA19.9, or a fragment thereof,
wherein the two or more tumor marker proteins are two or more different tumor marker proteins or are two or more different epitopes on the same tumor marker protein,
wherein the one or more tumor marker proteins prepared from a bodily fluid exhibit selective reactivity with cancer-associated anti-tumor autoantibodies, wherein the tumor marker proteins are over-expressed or altered forms of wild-type proteins,
wherein detection of complexes indicates the presence of cancer-associated anti-tumor autoantibodies in the patient, and
wherein a change in level of the anti-tumor autoantibodies in a sample after the anti-cancer treatment as compared to the level of the anti-tumor autoantibodies in a sample before the anti-cancer treatment indicates that the patient has responded positively to the treatment.

38. The method of claim 37 wherein the bodily fluid is ascites fluid, pleural effusion, seroma, hydrocoele or wound drainage fluid.

39. The method of claim 37 wherein the one or more tumor marker proteins that is MUC1, MUC16, c-myc, c-erbB2, p53, ras, BRCA1, BRCA2, APC, PSA, CEA or CA19.9, or a fragment thereof, is the one or more tumor marker proteins prepared from the bodily fluid.

40. The method of claim 37 wherein the one or more tumor marker proteins prepared from the bodily fluid are prepared by collecting bodily fluid from the body cavity or space in which a tumor is or was present from one or more cancer patients and isolating the tumor marker protein from the bodily fluid using protein purification techniques.

41. The method of claim 37 wherein the one or more tumor marker proteins prepared from the bodily fluid are prepared by collecting bodily fluid from the body cavity or space in which a tumor is or was present from two or more cancer patients, pooling the bodily fluid and isolating the tumor marker protein from the pooled bodily fluid using protein purification techniques.

42. The method of claim 40 wherein the isolated tumor marker protein is substantially immunoglobulin free.

43. The method of claim 37 where the bodily fluid from which the one or more tumor marker proteins is prepared is not whole blood or serum.

44. The method of claim 37 wherein the bodily fluid is produced during the disease process in response to or as a consequence of the presence of tumor cells.

45. The method of claim 37 wherein the cancer patient from which the tumor-induced bodily fluid is prepared is the same as the individual from which the sample was obtained.

46. A method of detecting recurrent disease in a patient in need of detection of a recurrent disease, comprising:
contacting a bodily fluid sample from the patient, wherein the patient was previously diagnosed as having cancer and has undergone anti-cancer treatment to reduce amount of cancer with an immunoassay reagent, and detecting a presence of complexes formed by specific binding of the immunoassay reagent to any cancer-associated anti-tumor autoantibodies present in the sample, wherein the immunoassay reagent comprises a panel of two or more tumor marker proteins, one or more of which having been prepared from a tumor-induced bodily fluid produced in a body cavity or space in the presence of the tumor of one or more cancer patients, wherein the bodily fluid contains more cancer-associated forms of the tumor marker protein than a non-tumor-induced bodily fluid in the same patient, and the bodily fluid is not a fluid derived from the systemic circulation, wherein at least one of the two or more tumor marker proteins is MUC1, MUC16, c-myc, c-erbB2, p53, ras, BRCA1, BRCA2, APC, PSA, CEA or CA19.9, or a fragment thereof, wherein the two or more tumor marker proteins are two or more different tumor marker proteins or are two or more different epitopes on the same tumor marker protein, wherein the one or more tumor marker proteins prepared from a bodily fluid exhibit selective reactivity with cancer-associated anti-tumor autoantibodies, wherein the tumor marker proteins are over-expressed or altered forms of wild-type proteins, wherein detection of complexes indicates the presence of cancer-associated anti-tumor autoantibodies in the individual, and wherein presence of an increased level of autoantibodies in the patient, as compared to a normal control, indicates that the cancer has recurred.

47. The method of claim 46 wherein the bodily fluid is ascites fluid, pleural effusion, seroma, hydrocoele or wound drainage fluid.

48. The method of claim 10 wherein the one or more tumor marker proteins that is MUC1, MUC16, c-myc, c-erbB2, p53, ras, BRCA1, BRCA2, APC, PSA, CEA or CA19.9, or a fragment thereof, is the one or more tumor marker proteins prepared from the bodily fluid.

49. The method of claim 46 wherein the one or more tumor marker proteins prepared from the bodily fluid are prepared by collecting bodily fluid from the body cavity or space in which a tumor is or was present from one or more cancer patients and isolating the tumor marker protein from the bodily fluid using protein purification techniques.

50. The method of claim 46 wherein the one or more tumor marker proteins prepared from the bodily fluid are prepared by collecting bodily fluid from the body cavity or space in which a tumor is or was present from two or more cancer patients, pooling the bodily fluid and isolating the tumor marker protein from the pooled bodily fluid using protein purification techniques.

51. The method of claim 49 wherein the isolated tumor marker protein is substantially immunoglobulin free.

52. The method of claim 46 where the bodily fluid from which the one or more tumor marker proteins is prepared is not whole blood or serum.

53. The method of claim 46 wherein the bodily fluid is produced during the disease process in response to or as a consequence of the presence of tumor cells.

54. The method of claim 46 wherein the cancer patient from which the tumor-induced bodily fluid is prepared is the same as the individual from which the sample was obtained.

* * * * *